United States Patent
Kelly et al.

(10) Patent No.: US 10,087,121 B2
(45) Date of Patent: Oct. 2, 2018

(54) PRODUCTION OF HYDROCARBON LIQUIDS

(71) Applicants: Karen Sue Kelly, Burlington (CA); Larry Jack Melnichuk, Burlington (CA)

(72) Inventors: Karen Sue Kelly, Burlington (CA); Larry Jack Melnichuk, Burlington (CA)

(*) Notice: Subject to any disclaimer, the term of this patent is extended or adjusted under 35 U.S.C. 154(b) by 0 days.

(21) Appl. No.: 15/433,245

(22) Filed: Feb. 15, 2017

(65) Prior Publication Data
US 2018/0002248 A1 Jan. 4, 2018

Related U.S. Application Data

(63) Continuation of application No. 14/555,765, filed on Nov. 28, 2014, now abandoned, which is a
(Continued)

(51) Int. Cl.
C07C 1/04 (2006.01)
C07C 1/12 (2006.01)
(Continued)

(52) U.S. Cl.
CPC .......... C07C 1/22 (2013.01); C01B 3/32 (2013.01); C01B 3/323 (2013.01); C01B 3/382 (2013.01);
(Continued)

(58) Field of Classification Search
CPC .......... C07C 1/04; C07C 1/12; C10G 1/00
(Continued)

(56) References Cited

U.S. PATENT DOCUMENTS 4,110,359 A 8/1978 Marion
4,481,305 A 11/1984 Jorn et al.
(Continued)

FOREIGN PATENT DOCUMENTS

| CA | 1117061 A1 | 1/1982 |
|---|---|---|
| EP | 1391496 A1 | 2/2004 |
| WO | 2007123510 A1 | 11/2007 |

OTHER PUBLICATIONS

"Biomass Gasification" Anil Rajvanshi; 1986, pp. 1-21.*
(Continued)

Primary Examiner — Thuan D Dang

(57) ABSTRACT

A process to efficiently convert organic feedstock material into liquid non-oxygenated hydrocarbons in the $C_5$ to $C_{12}$ carbon skeleton range is disclosed. The process can utilize gaseous, liquid or solid organic feedstocks containing carbon, hydrogen and, optionally, oxygen. The feedstock may require preparation of the organic feedstock for the process and is converted first into a synthesis gas containing carbon monoxide and hydrogen. The synthesis gas is then cleaned and conditioned and extraneous components removed, leaving substantially only the carbon monoxide and hydrogen. It is then converted via a series of chemical reactions into the desired liquid hydrocarbons. The hydrocarbons are suitable for combustion in a vehicle engine and may be regarded a replacement for petrol made from fossil fuels in the $C_5$ to $C_{12}$ carbon backbone range. The process also recycles gaseous by-products back through the various reactors of the process to maximize the liquid hydrocarbon in the $C_5$ to $C_{12}$ carbon skeleton range yield.

19 Claims, 3 Drawing Sheets

Related U.S. Application Data continuation of application No. 12/988,765, filed as application No. PCT/CA2009/000518 on Apr. 17, 2009, now abandoned.

(60) Provisional application No. 61/124,896, filed on Apr. 21, 2008.

(51) Int. Cl.

| | | |
|---|---|---|
| *C07C 1/22* | (2006.01) | |
| *C01B 3/32* | (2006.01) | |
| *C10G 3/00* | (2006.01) | |
| *C10K 1/00* | (2006.01) | |
| *C10J 3/46* | (2006.01) | |
| *C10K 1/10* | (2006.01) | |
| *C07C 41/01* | (2006.01) | |
| *C10G 2/00* | (2006.01) | |
| *C01B 3/38* | (2006.01) | |
| *C10K 3/04* | (2006.01) | |
| *C01B 3/52* | (2006.01) | |
| *C10K 1/02* | (2006.01) | |
| *C01B 3/48* | (2006.01) | |
| *C10J 3/54* | (2006.01) | |
| *C01B 3/50* | (2006.01) | |

(52) U.S. Cl.
CPC .............. *C01B 3/48* (2013.01); *C01B 3/50* (2013.01); *C01B 3/52* (2013.01); *C07C 41/01* (2013.01); *C10G 2/334* (2013.01); *C10G 3/49* (2013.01); *C10G 3/52* (2013.01); *C10J 3/46* (2013.01); *C10J 3/463* (2013.01); *C10J 3/54* (2013.01); *C10K 1/007* (2013.01); *C10K 1/02* (2013.01); *C10K 1/10* (2013.01); *C10K 3/04* (2013.01); *C01B 2203/025* (2013.01); *C01B 2203/0244* (2013.01); *C01B 2203/0283* (2013.01); *C01B 2203/04* (2013.01); *C01B 2203/048* (2013.01); *C01B 2203/0415* (2013.01); *C01B 2203/0475* (2013.01); *C01B 2203/062* (2013.01); *C01B 2203/0894* (2013.01); *C01B 2203/1058* (2013.01); *C07C 2529/06* (2013.01); *C10G 2300/1014* (2013.01); *C10G 2300/1018* (2013.01); *C10G 2300/1022* (2013.01); *C10G 2300/4081* (2013.01); *C10G 2400/02* (2013.01); *C10G 2400/22* (2013.01); *C10G 2400/30* (2013.01); *C10J 2300/092* (2013.01); *C10J 2300/1238* (2013.01); *C10J 2300/1656* (2013.01); *Y02P 30/20* (2015.11); *Y02P 30/48* (2015.11)

(58) Field of Classification Search
USPC ................. 585/240–242, 310, 733
See application file for complete search history.

(56) References Cited

U.S. PATENT DOCUMENTS

| | | | |
|---|---|---|---|
| 4,788,369 A | 11/1988 | Marsh et al. | |
| 4,857,559 A * | 8/1989 | Eri ................. | B01J 23/8896 518/700 |
| 5,459,166 A * | 10/1995 | Lee ................. | C10G 2/33 518/700 |
| 5,602,289 A | 2/1997 | Dijk | |
| 6,211,254 B1 * | 4/2001 | Whitney ........... | C07C 29/1518 252/373 |
| 6,749,828 B1 * | 6/2004 | Fukunaga ........ | B01J 21/066 252/373 |
| 7,294,225 B2 | 11/2007 | Lindblom | |
| 2004/0220285 A1 * | 11/2004 | Boerrigter ........ | C10K 1/18 518/726 |
| 2005/0250862 A1 | 11/2005 | Bayle et al. | |
| 2006/0014841 A1 | 1/2006 | Melnichuk et al. | |
| 2009/0259076 A1 | 10/2009 | Simmons et al. | |

OTHER PUBLICATIONS

Examiner's Report issued in Canadian Application serial No. 2,738,270, dated Oct. 25, 2012.
Examiner's Report issued in Canadian Application serial No. 2,738,270, dated Sep. 26, 2014.
International Preliminary Report on Patentability for application serial No. PCT/CA2009/000518, dated Apr. 20, 2010.
International Search Report for application serial No. PCT/CA2009/000518, dated Aug. 12, 2009.
Notice of Allowance for CA 2,738,270, dated Dec. 11, 2014.
Office Action issued in U.S. Appl. No. 12/988,765, dated Dec. 11, 2012.
Office Action issued in U.S. Appl. No. 12/988,765, dated Jun. 11, 2014.
Office Action issued in U.S. Appl. No. 12/988,765, dated Sep. 18, 2013.
Written Opinion for application serial No. PCT/CA2009/000518, dated Aug. 12, 2009.
Hutchinson F. How does Gasification differ from combustion? About Gasification 2004-2009 http://www.clean-energy.us/facts/gasification.htm.
Kolesnichenko, N.V., et al., entitled "Synthesis of Gasoline From Syngas via Dimethyl Ether", Kinetics and Catalysis, vol. 48, No. 6, Sep. 30, 2007, pp. 789-793.
Mills et al., entitled "Status and Future Opportunities for Conversion of Synethis Gas to Liquids Fuels", Fuel, IPC Science and Technology Press Guildford, GB, vol. 73., No. 8, Aug. 1, 1994, pp. 1243-1279.
Supplement European Search Report for EP 09735166.2 (PCT/CA2009/000518), dated Dec. 17, 2013.
Written Opinion for EP 09735166.2 (PCT/CA2009/000518), dated Jan. 8, 2014.

\* cited by examiner

PRODUCTION OF HYDROCARBON LIQUIDS

RELATED APPLICATIONS

The present application is Continuation application of U.S. application Ser. No. 12/988,765, entitled "Production of Hydrocarbon Liquids" filed Mar. 8, 2011, which is the National Phase Entry of International Patent Application serial number PCT/CA2009/000518, entitled "Production of Hydrocarbon Liquids" and filed Apr. 17, 2009, which in turn claims priority to U.S. Provisional Application Ser. No. 61/124,896 entitled "A Process for Producing Gasoline From Carbonaceous Feedstock", filed Apr. 21, 2008, the subject matter of which is herein incorporated by reference.

FIELD

The present invention is related to a process for producing hydrocarbons for use as a fuel. Specifically, the present invention is related to the production of non-oxygenated hydrocarbons having a $C_5$ to $C_{12}$ carbon skeleton produced via a dimethyl ether catalytic reaction from synthesis gas.

BACKGROUND

Fuel for vehicles has been produced in the past from the refining of crude oil. The refining process results in gasoline, jet fuel and diesel fuel. This source has been the mainstay of fuel for our transportation systems since the 1800s.

In 1955, synthetic oil was first produced from coal by Sasol, a South African group of companies in their Sasolburg plant, where it continues today. In the early 1950s Sasol pioneered the use of Fischer-Tropsch (F-T) catalysts, which converted the coal into fuels and chemicals. In particular, the Fischer-Tropsch process produces synthetic diesel fuel. To achieve the conversion, Sasol began to gasify the coal, a technology which is used today to produce synthesis gas, a mixture of predominantly carbon monoxide and hydrogen. The synthesis gas, as produced by via the Fischer-Tropsch process continues to be utilized for diesel fuel throughout the world, or as a feedstock for methanol production in areas which do not have a natural gas supply.

Over the years, variations on the process pioneered by Sasol have arisen from the original Fischer-Tropsch catalysts. Their major limitation is that they do not produce gasoline mixtures, only predominantly diesel-range mixtures, those being mostly paraffinic and aromatic hydrocarbons with a $C_{10}$ to $C_{15}$ carbon skeleton. Much research and effort has been undertaken to modify the original Fischer-Tropsch process to produce the gasoline-range mixtures, those having a $C_5$ to $C_{12}$ carbon skeleton, but to no avail.

More recently, under pressure from the global oil crisis, there has been concerted effort in the U.S. to develop chemical pathways to produce gasoline that do not involve Fischer-Tropsch catalysts. Modified methanol-production catalysts have been attempted, and the most promising routes involve the conversion of methanol into gasoline-range products. This work is largely theoretical and conducted by the large government-funded laboratories and universities.

A process to efficiently convert synthesis gas from any carbon-derived source to gasoline is urgently needed to solve the reduction in crude oil availability. The most rational route to gasoline is through conversion of organic, non-fossil, material such as biomass into synthesis gas. It is desirable to develop a process which allows for the energetically efficient conversion of synthesis gas into non-oxygenated hydrocarbons having a $C_5$ to $C_{12}$ carbon skeleton, for example, gasoline.

Researchers have investigated the conversion of synthesis gas into gasoline using specialized bacteria. However, this route is not as desirable as a chemical synthesis route because the bacterial culturing, care and feeding of the converting bacteria is more art than science. The process is similar to the production of ethanol through yeast, in that the bacteria must be kept in special heated vats, supplied with specific types and concentrations of synthesis gas and the resultant products must be continuously removed. As a further disadvantage to this route of gasoline synthesis, there are large thermal inefficiencies owing to the large amount of water which must be externally heated as required to complete the process and maintain the bacteria.

Therefore, it is highly desirable to develop a chemical route to gasoline carbon-range products which uses more energetically efficient routes of synthesis and one in which there is an abundance of inexpensive starting material. In order to make the process as efficient as possible, it is desirable to develop and utilize appropriate catalysts to maintain the number of process steps as low as possible, recycle by-products and un-reacted compounds from the various steps in the process back into the reactors to be re-reacted, and on which enables the production of relatively pure products in each reactor to be used in the process such that the next reactor in the process can run as efficiently as possible.

SUMMARY

At least one of the needs and objectives that will become apparent from the following description is achieved in the present invention which comprises a process for producing substantially $C_5$ to $C_{12}$ alkanes, alkenes and aromatics for use in a fuel. The present invention comprises a process for producing useful gases and liquid hydrocarbons from organic, thus carbon-containing, materials.

In at least one embodiment of the present invention, the process for producing a $C_5$ to $C_{12}$ hydrocarbon fuel from organic sources comprises providing an organic feedstock to produce a synthesis gas stream therefrom containing at least carbon monoxide, carbon dioxide and hydrogen and substantially removing unwanted solid matter comprising oxides, ash and hydrocarbons having a carbon skeleton of greater than $C_{10}$ from the synthesis gas to produce a first cleaned synthesis gas stream. The first cleaned synthesis gas stream is then compressed to substantially remove water and then conditioned and further cleaned to substantially remove inorganic elements and inorganic compounds to produce a second cleaned synthesis gas stream containing at least carbon monoxide, carbon dioxide and hydrogen. Carbon dioxide is selectively removed from the second cleaned synthesis gas stream and the second cleaned synthesis gas stream is then catalytically treated to produce a first mixture containing at least carbon monoxide, hydrogen and dimethyl ether. The dimethyl ether is collected from the first mixture and catalytically reacted produce a second mixture containing at least alkanes, alkenes, napthalenes and aromatics. The at least alkanes having from a $C_5$ to a $C_{12}$ skeleton are collected from the second mixture to provide a hydrocarbon fuel from the initial organic feedstock.

Furthermore, according one aspect of the invention, in certain embodiments of the present invention, light oils and tars produced as a by-product of the process of the present invention, may be recycled back through the process to the gasifier and converted into the synthesis gas stream to produce carbon monoxide, carbon dioxide and hydrocarbons to be used in the formation of dimethyl ether.

In yet another aspect of the invention, at various stages of the process outlined above, in certain embodiments, hydrocarbons, carbon monoxide, carbon dioxide and hydrogen gas may optionally be recycled back through the process into the first cleaned synthesis gas stream to be used to produce additional dimethyl ether.

In yet another aspect of the invention, the organic material is partially oxidized thereby producing a gas stream. The gas stream is cleaned of particulate matter, and light oils and tars are removed. The gases are then compressed and passed into a reactor to convert any hydrocarbon gases such as alkanes, alkenes or alkynes present into carbon monoxide and hydrogen. The converted gases are then compressed further and the carbon dioxide removed. Following this step the gases are then catalytically reacted to form dimethyl ether. The dimethyl ether is then introduced to another reactor to produce non-oxygenated species of carbon compounds, gases plus water.

In another embodiment of the present invention, a process for producing a $C_5$ to $C_{12}$ hydrocarbon fuel from organic material is provided. An organic feedstock suitable for producing a synthesis gas stream from the feedstock containing at least carbon monoxide, carbon dioxide and hydrogen is provided. The synthesis gas stream containing at least carbon monoxide, carbon dioxide and hydrogen is processed to substantially remove unwanted solid and liquid matter comprising oxides, ash and hydrocarbons having a carbon skeleton of greater than $C_{10}$ from the synthesis gas stream to produce a first cleaned synthesis gas stream containing at least carbon monoxide, carbon dioxide and hydrogen. The first cleaned synthesis is treated to substantially remove water and inorganic elements and inorganic compounds from the first cleaned synthesis stream to provide a second cleaned synthesis gas stream containing at least carbon monoxide, carbon dioxide and hydrogen. At least a portion of alkanes, alkenes and alkynes are separated from the second cleaned synthesis gas stream and reacted to produce substantially carbon monoxide, carbon dioxide and hydrogen in a reformer. The carbon monoxide, carbon dioxide and hydrogen from the reformer is joined back into said second cleaned synthesis gas stream and processed again to convert at least some of the carbon monoxide into carbon dioxide and water. Carbon dioxide is then selectively removed from the second cleaned synthesis gas stream and the partially converted second cleaned synthesis gas stream is catalytically treated to produce a first mixture containing at least carbon monoxide, hydrogen and dimethyl ether. The dimethyl ether is collected from the first mixture and catalytically reacted to produce a second mixture containing at least alkanes. The mixture containing at least alkanes having between a $C_5$ to a $C_{12}$ carbon backbone are selectively obtained from the second mixture.

In another embodiment of the present invention, a process for producing a $C_5$ to $C_{12}$ hydrocarbon fuel from a synthesis gas is provided wherein the ratio of hydrogen to carbon monoxide in the second cleaned synthesis gas is adjusted in a water/gas shift reactor to be between from about 1:1 to about 1:2.

In another embodiment of the present invention, a process for producing a $C_5$ to $C_{12}$ hydrocarbon fuel from a synthesis gas is provided. A synthesis gas stream is provided and carbon dioxide is selectively removed from the synthesis gas stream. The synthesis gas stream is then catalytically treated to produce a first mixture containing at least carbon monoxide, hydrogen and dimethyl ether. The dimethyl ether is then collected from the first mixture and catalytically reacted to produce a second mixture containing at least alkanes. The second mixture containing at least alkanes having from a $C_5$ to a $C_{12}$ skeleton are selectively obtained from said second mixture.

In still yet another aspect of the invention, liquid non-oxygenated hydrocarbons in the $C_5$ to $C_{12}$ carbon skeleton range are produced from an organic feedstock comprising the steps of partially oxidizing organic feedstock to produce a gas stream containing at least carbon monoxide, hydrogen, carbon dioxide and hydrocarbons such as alkanes, alkenes or alkynes. The gas stream is cleaned to substantially remove particulate matter and any contaminants or oxidizers. The cleaned gas stream is then compressed which substantially removes water vapour and cleaned again to substantially remove contaminants such as metals or oxidizers. The gas stream is then split to separate the hydrocarbons from carbon monoxide, hydrogen and carbon dioxide. The separated hydrocarbons are reacted to produce carbon monoxide, carbon dioxide and hydrogen. The newly produced carbon monoxide, carbon dioxide and hydrogen is then re-introduced to the cleaned gas stream and reacted with steam in a water/gas shift reactor, compressed and the resultant carbon dioxide is substantially removed. The gas stream with carbon dioxide substantially removed is then catalytically reacted to produce a mixture of substantially dimethyl ether as well as carbon monoxide, carbon dioxide and hydrogen, water and methanol. The carbon monoxide, carbon dioxide and hydrogen are recycled back through the water/shift reactor. Resultant methanol is recycled to be catalytically reacted to form dimethyl ether. Water is removed. The dimethyl ether is catalytically reacted to produce liquid hydrocarbons and water. The liquid hydrocarbons are separated from the water to obtain a mixture of $C_5$ to $C_{12}$ carbon skeleton hydrocarbons.

In another aspect, there is provided a process for producing a $C_5$ to $C_{12}$ hydrocarbon fuel from organic material. The process comprising:

a) applying a heat source to heat an organic feedstock and oxygen at substoichiometric conditions to a temperature sufficient for partial combustion of the organic feedstock to occur and then ceasing application of the heat source once partial combustion has commenced;

b) partially combusting the organic feedstock so as to produce a synthesis gas stream, the synthesis gas stream containing at least carbon monoxide, carbon dioxide and hydrogen;

c) substantially removing unwanted solid and liquid matter comprising oxides, ash and hydrocarbons having a carbon skeleton of greater than $C_{10}$ from the synthesis gas stream to produce a first cleaned synthesis gas stream containing at least carbon monoxide, carbon dioxide and hydrogen;

d) compressing the first cleaned synthesis gas stream and substantially removing water;

e) conditioning and further cleaning the first cleaned synthesis gas stream by substantially removing inorganic elements and inorganic compounds from the first cleaned synthesis gas stream to provide a second cleaned synthesis gas stream containing at least carbon monoxide, carbon dioxide and hydrogen;

f) selectively removing carbon dioxide from the second cleaned synthesis gas stream;

g) catalytically treating the second cleaned synthesis gas stream to produce a first mixture containing at least carbon monoxide, hydrogen and dimethyl ether;

h) collecting the dimethyl ether from the first mixture;
i) catalytically reacting the dimethyl ether to produce a second mixture containing at least alkanes; and
j) selectively obtaining the alkanes having from a $C_5$ to $C_{12}$ skeleton from the second mixture.

In another aspect, there is provided a process for producing a $C_5$ to $C_{12}$ hydrocarbon fuel from organic material comprising:
a) applying a heat source to heat an organic feedstock and oxygen at substoichiometric conditions up to a temperature of about 800° C. and then ceasing application of the heat source once partial combustion in an exothermic reaction has commenced;
b) partially combusting the organic feedstock without continuous application of an external heat source so as to produce a synthesis gas stream, the synthesis gas stream containing at least carbon monoxide, carbon dioxide and hydrogen;
c) substantially removing unwanted solid and liquid matter comprising oxides, ash and hydrocarbons having a carbon skeleton of greater than $C_{10}$ from the synthesis gas stream to produce a first cleaned synthesis gas stream containing at least carbon monoxide, carbon dioxide and hydrogen;
d) compressing the first cleaned synthesis gas stream and substantially removing water;
e) removing at least a portion of any alkanes, alkenes and alkynes from the first cleaned synthesis gas stream;
f) reacting the removed alkanes, alkenes and alkynes of step e) with a catalyst to produce a supplemental gas stream containing at least carbon monoxide, carbon dioxide and hydrogen;
g) removing inorganic elements and inorganic compounds from the first cleaned synthesis gas stream to provide a second cleaned synthesis gas stream containing at least carbon monoxide, carbon dioxide and hydrogen;
h) merging the second cleaned synthesis gas stream with the supplemental gas stream;
i) selectively removing carbon dioxide from the second cleaned synthesis gas stream merged with the supplemental gas stream;
j) catalytically treating the second cleaned synthesis gas stream merged with said supplemental gas stream to produce a first mixture containing at least carbon monoxide, hydrogen and dimethyl ether;
k) collecting the dimethyl ether from the first mixture;
l) catalytically reacting the dimethyl ether to produce a second mixture containing at least alkanes; and
m) selectively obtaining the alkanes having from a $C_5$ to $C_{12}$ skeleton from the second mixture.

In yet another aspect, there is provided a process for producing a $C_5$ to $C_{12}$ hydrocarbon fuel from organic material comprising:
a) forming a first synthesis gas stream by the steps of:
  i) applying a heat source to heat an organic feedstock and oxygen at substoichiometric conditions up to a temperature of about 800° C. and then ceasing application of the heat source once partial combustion in an exothermic reaction has commenced,
  ii) partially combusting the organic feedstock without continuous application of a heat source so as to produce a synthesis gas stream, the synthesis gas stream containing at least carbon monoxide, carbon dioxide and hydrogen,
  iii) substantially removing unwanted solid and liquid matter comprising oxides, ash and hydrocarbons having a carbon skeleton of greater than $C_{10}$ from the synthesis gas stream to produce a first cleaned synthesis gas stream containing at least carbon monoxide, carbon dioxide and hydrogen;
  iv) recycling and enjoining the hydrocarbons having a carbon skeleton greater than $C_{10}$ to step a)(ii) for partial combustion,
  v) compressing the first cleaned synthesis gas stream and substantially removing water, and
  vi) removing at least a portion of any alkanes, alkenes and alkynes from the first cleaned synthesis gas stream;
b) forming a second cleaned synthesis gas stream by the steps of:
  i) reacting the removed alkanes, alkenes and alkynes of step a)(vi) with a catalyst to produce at least carbon monoxide, carbon dioxide and hydrogen, and
  ii) selectively removing carbon dioxide from the second cleaned synthesis gas stream;
c) merging the first cleaned synthesis gas stream and the second cleaned synthesis gas stream so as to provide a merged cleaned synthesis gas stream;
d) catalytically treating the merged synthesis gas stream to produce a first mixture containing at least carbon monoxide, hydrogen and dimethyl ether;
e) collecting the dimethyl ether from the first mixture and recycling the carbon monoxide back into the second cleaned synthesis gas stream for additional catalytic treatment;
f) catalytically reacting the dimethyl ether to produce a second mixture containing at least alkanes; and
g) selectively obtaining the alkanes having from a $C_5$ to $C_{12}$ skeleton from the second mixture.

DETAILED DESCRIPTION

The present invention relates a process for converting organic materials into non-oxygenated hydrocarbons. The process, as described herein, has broad application, but is particularly useful for the production of alternatives to fossil fuels, more particularly, to non-oxygenated liquid $C_5$ to $C_{12}$ hydrocarbon compounds suitable for use as a fuel for combustion in motor vehicle engines. It will be appreciated that the $C_5$ to $C_{12}$ hydrocarbon compounds produced via the process as described herein may have other uses beyond that of combustion fuel. For example, the $C_5$ to $C_{12}$ hydrocarbon compounds produced by the process as described herein may also be suitable for, by way of non-limiting examples, use as lubricants and organic solvents and the like.

The following presents a simplified summary of the general inventive concept herein to provide a basic understanding of some aspects of the invention. This summary is not an extensive overview of the invention. It is not intended to restrict key or critical elements of the invention or to delineate the scope of the invention beyond that explicitly or implicitly described by the following description and claims.

It is to be understood that the phraseology and terminology used herein is for the purpose of description and should not be regarded as limiting. The use of "including," "comprising," "containing," or "having" and variations thereof herein is meant to encompass the items listed thereafter and equivalents thereof as well as additional items.

As used herein, term "organic materials" refers to matter derived from once-living organisms, capable of decay or are the products of decay, or those which are composed of organic compounds. Furthermore, as used herein, the term "organic compounds" are defined as those which contain carbon. Biomass is a subset of organic materials. As used herein, the terms "organic material" or "organic materials" comprises biomass, organic compounds, organic feedstock and the like.

As used herein, the term "organic feedstock" makes reference to organic material comprising organic compounds. Biomass, used to produce organic feedstock, suitable for the purposes of this disclosure are, by way of non-limiting examples, vegetative matter, such grasses, grains, reeds, coniferous plants, deciduous plants, agricultural matter and waste or by-products thereof, animal matter and waste or by-products thereof, and organic portions of municipal or industrial garbage. Furthermore, for the purposes of the present disclosure, by way of non-limiting examples, landfill material such as that comprising hydrocarbons, for example, plastics, rubbers and oils may also be considered suitable for use as organic feedstock and thus comprise organic material. For the purposes of various embodiments of the present disclosure, the organic feedstock may be provided as a solid, a semi-solid, a gas, or a liquid or combinations thereof.

Figure 1:
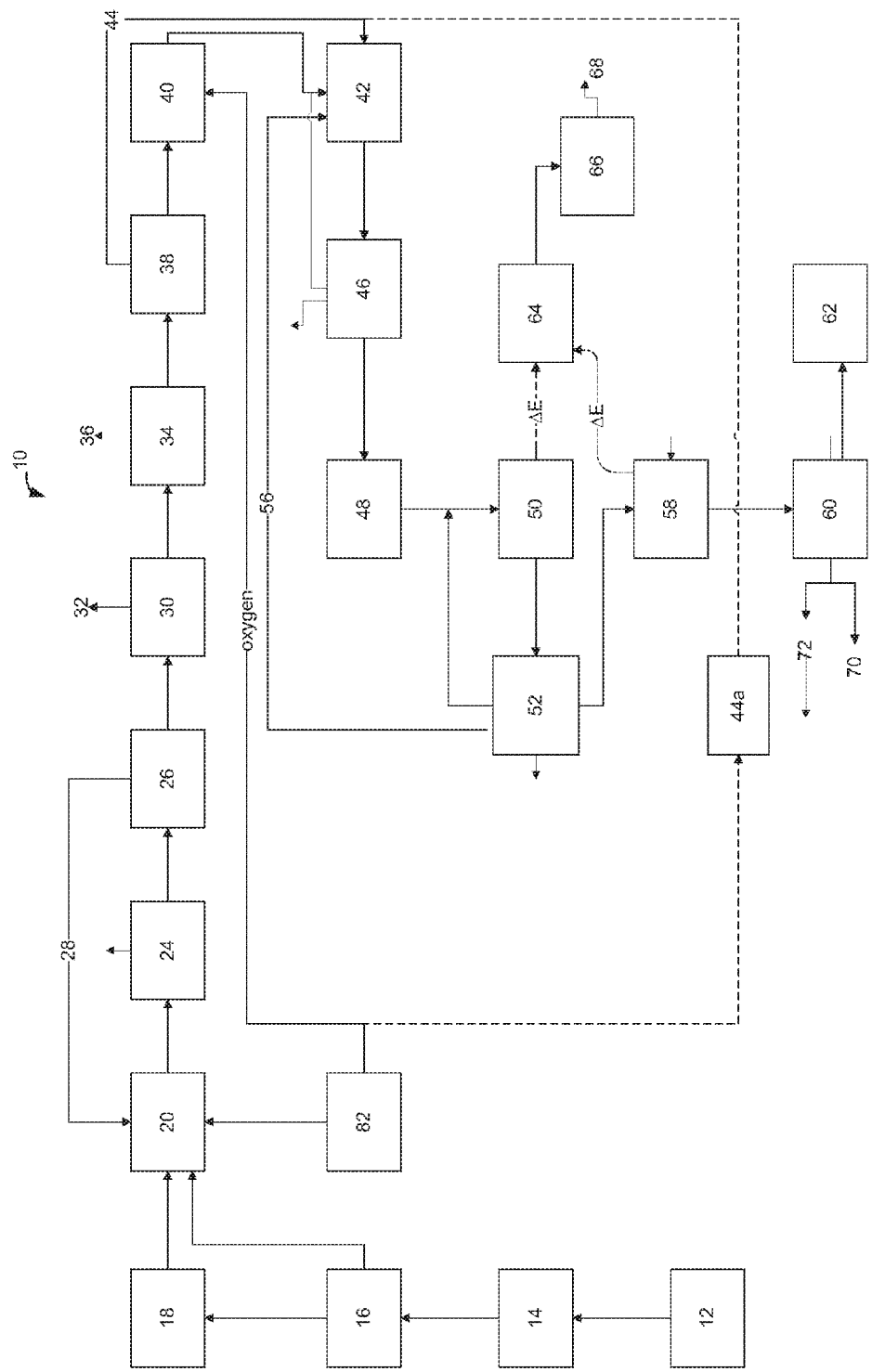
FIG. 1 is schematic block diagrammatical representation of an embodiment of the process of the present invention starting from solid or semi-solid organic feedstock.

With reference to FIG. 1 the process is generally described at 10. An organic material feedstock, henceforth referred to as "organic feedstock", denoted at 12 is processed to reduce the size of the starting organic matter to smaller particles at 14 as seen in the block diagram. For the purposes of explanation and description, wood is used in the following description as organic feedstock 12. However, any organic feedstock may used as provided by the description of organic feedstock as noted in the description above. As an optional step, provided at 16, the starting organic feedstock 12, may, if necessary be dried to reduce the moisture content of the organic feedstock 12 to a suitable level for the production of synthesis gas 74. The drying process 16 may be provided by conventional means as known following particle size reduction 14. For example, the organic feedstock 12, being reduced in size at 14, may be dried by kiln drying, desiccation, air-drying or any other suitable method. If the organic feedstock does not require drying, that is that moisture content of the organic feedstock 12 is suitable for introduction of the organic feedstock 12 into gasifier 20 as processed in 14, steam from a boiler system 114 is provided and the steam and organic feedstock 12 from 14 is introduced to the gasifier reactor 20. As indicated above, should drying of the organic feedstock 12 as processed at 14 be necessary, the dried organic feedstock from 16 is introduced to a surge bin 18. The dried organic feedstock from 16 is stored in the surge bin 18 and kept air-free by the addition of a blanket of inert gas, which may be carbon dioxide removed at 14.

Once the organic feedstock 12 from either 14 or 18 is introduced into the gasifier 20, oxygen from an oxygen generator 22 is supplemented as required into the gasifier 20 to aid in the partial combustion of the organic feedstock 12.

The gasifier 20 serves the primary function of partially combusting the organic feedstock 12 to produce a synthesis gas 74, comprising at least carbon monoxide, carbon dioxide, hydrogen, and alkanes. Dependant upon of the composition of the original organic feedstock 12, the synthesis gas 74 produced by partial combustion of the organic feedstock 12 in the gasifier 20 may also comprise, for example, particulate matter, such as a solid matter, sulfur and sulfur compounds, halides and halide compounds, and other compounds or matter resulting from the synthesis gas 74 generation in the gasifier 20.

The synthesis gas 74 from the gasifier 20 is then introduced to, preferably, a cyclone-type cleaning system 24 to remove solid matter 117 from the synthesis gas 74. The cleaning system at 24 need not be cyclone-type system per se. Any system suitable for removing unwanted solid particulate matter from the synthesis gas 74 may be used, for example, a sieve-type system, a vacuum-type system, by bag houses and/or filters. Solid matter that it is desirable to remove at 24 is, for example, uncombusted organic feedstock particulate, metal oxides such as NiO, CuO, FeO and non-combustible debris contained within the organic feedstock 12 and not gasified in the gasifier 20. Exiting from the cyclone-type cleaning system 24 is a first cleaned synthesis gas stream 76 containing at least carbon monoxide, carbon dioxide and hydrogen. The first cleaned synthesis gas stream 76 is substantially devoid of solid matter. The first cleaned synthesis gas stream 76 may contain other elements and molecules, such as, for example sulfur, metals, metal oxides, halides, alkanes and other hydrocarbon molecules. At 26, a scrubber system is used to substantially remove light oils, olefins and tars generally having a carbon skeleton of greater than $C_{10}$. Furthermore, the scrubber system 26 substantially removes metal compounds such as, for example $NO_x$, $SO_x$ and Cl as well as other molecular impurities which may be present in the first cleaned synthesis gas stream 76. The scrubber system 26 is preferably a venturi-type system, however other types of systems as may be known in the art may be used.

The light oils, olefins and tars generally having a carbon skeleton of greater than $C_{10}$, in some embodiments of the invention are recycled back to the gasifier 20 to be partially combusted into synthesis gas 74 and moved through the system as described above. This recycling of unused combustible matter, such as light oils, olefins and tars generally having a carbon skeleton of greater than $C_{10}$ seeks to increase the amount of synthesis gas 74 that can be made per unit of organic feedstock 12 input and reduces usable waste thus increasing the efficiency of the overall reaction process with respect to the production of $C_5$ to $C_{12}$ hydrocarbons produced per unit of organic feedstock input 12.

The first cleaned synthesis gas stream 76, following scrubbing 26 is then introduced into a compressor at 30. In the compressor 30, the first cleaned synthesis gas stream 76 is compressed and water 32 substantially removed via condensation.

As is shown at 34 of FIG. 1, the now compressed first synthesis gas stream 76 is introduced into a guard bed 34, or a series of guard beds. The guard bed is a filter bed containing a catalyst, which is selected to remove the known impurity, thus conditioning and further cleaning the first cleaned synthesis gas stream. More than one bed may be required to remove multiple impurities. In the guard bed(s) 34, elemental impurities 36, such as sulfur are substantially removed to produce a second cleaned synthesis gas stream 78 exiting from the guard bed 34. It will be appreciated that other undesired impurities 36 may be removed by the guard bed 34. The second cleaned synthesis gas stream 78 comprises at least carbon monoxide, carbon dioxide, hydrogen and alkanes, and may under certain conditions further alkenes and alkynes. The second cleaned synthesis gas stream 78 is now substantially devoid of impurities and constituents not belonging to carbon monoxide, carbon dioxide, hydrogen and alkanes, or certain conditions, alkenes and alkynes. In certain embodiments, the second cleaned synthesis gas stream 78 is then introduced into an alkane separator 38 which substantially separates the alkanes and in certain conditions, alkenes and alkynes from the second cleaned synthesis gas 78. The alkanes, alkenes and alkynes from the alkane separator 38 are then introduced to a reformer reactor 40 wherein the alkanes, alkenes and alkynes are reacted to from carbon monoxide, carbon dioxide and hydrogen.

The second cleaned synthesis gas stream 78 is combined with oxygen and steam and flows into the alkane reformer 40 reaction vessel where at least methane and other alkanes, alkenes and alkynes are converted into carbon monoxide, carbon dioxide and hydrogen at high temperature according to the following reaction equations using a catalyst:

$$C_nH_m + nH_2O \rightarrow nCO + (m/2+n)H_2$$

$$C_nH_m + nO_2 \rightarrow nCO_2 + (m/2+n)H_2$$

The preferred alkane reactor is an autothermal reactor (ATR), which consists of a fixed bed reactor where the reforming takes place. The second cleaned synthesis gas stream 78, oxygen from the oxygen generator 22 and steam (not shown) flow into a mixer/burner inside the reformer. In the combustion chamber, partial combustion reactions take place, followed by steam reforming reactions and shift conversions to equilibrium over the catalyst bed. The overall reaction is exothermic, resulting in high outlet temperatures, typically 950-1100° C. The pressure may be high, up to 100 bar (9790 kPa). Soot-free operation is achieved through optimized burner design and by catalytic conversion of soot precursors over the catalyst bed. The metal-based catalyst in the reformer reactor 40 promotes the above conversion. The catalyst, preferably a nickel catalyst, is dispersed on a support material, preferably magnesium aluminum oxide, $MgAl_2O_4$ within the reformer reactor 40. Other suitable catalysts may be used. It will be appreciated that other support materials could alternatively be used in the reformer reactor 40.

According to the currently disclosed process, both gaseous hydrogen and carbon monoxide are required for the production of dimethyl ether, which is an intermediate step in the production of $C_5$ to $C_{12}$ hydrocarbons 85. A function of the alkane reformer reactor 40 in the currently disclosed process is to convert substantially all hydrocarbon compounds within the second synthesis gas stream 78 into carbon monoxide and hydrogen gases. The residence time of the carbon monoxide and hydrogen gas in the alkane reformer reactor 40 is sufficient for complete conversion; however other retention times may be realized in optimization of the disclosed process respective to individual process set-ups.

Within the alkane reformer reactor 40, at least a portion of the resulting carbon monoxide is further oxidized to carbon dioxide. The proper balancing of carbon monoxide and hydrogen for downstream dimethyl ether and ultimately $C_5$ to $C_{12}$ alkanes 85 production is accomplished by the water/gas shift reactor 42, as discussed below.

Additionally, it will be appreciated that the minimization of carbon formation within the alkane reformer reactor 40 is necessary in order to maximize the effective life of the catalyst material. Reactor operating conditions of temperature, pressure, and steam content all affect carbon formation. As such, prior to entering an alkane reformer reactor 40, a synthesis gas should be conditioned so as to reduce or remove compounds that will decrease the effectiveness of the catalytic reaction. The alkane reformer catalyst is especially sensitive to sulfur compounds. Hence, in preceding steps of the currently disclosed process, the conditioning of the synthesis gas is discussed with respect to a first cleaned synthesis gas stream 76 and a second cleaned synthesis gas stream 78.

The alkane reformer reactor 40 is preferably an autothermal reformer; however any suitable reformer may be used. Furthermore, reaction conditions in the reformer 40 are carried-out at from about 420° C. to about 500° C. and at a pressure of about 75 psi to about 200 psi (about 524 kPa to about 1398 kPa), dependent the reformer's manufacture's guidelines. The reaction conditions are adjusted to maintain the optimal space velocity of the reaction. The carbon monoxide, carbon dioxide, and hydrogen from the alkane separator 38 and the carbon monoxide, carbon dioxide and/or hydrogen resultant from the reaction of the alkanes in the alkane reformer reactor 40 are combined or introduced independently into a water/gas shift reactor 42.

The water/gas shift reactor 42 is utilized to convert carbon monoxide and water into hydrogen and carbon dioxide at moderate temperatures.

The reaction inside the water/gas shift reaction proceeds according to the following reaction with the aid of a catalyst:

$$CO + H_2O \rightarrow CO_2 + H_2$$

A base metal catalyst, preferably a nickel catalyst, dispersed in a support material, preferably aluminum oxide, $Al_2O_3$ within the water/gas shift reactor 42, is suitably used. Other suitable catalysts may be transition metals, Pt—$CeO_2$, or Raney copper catalysts. It will be appreciated that other support materials, such as for example, zinc oxide could alternatively be used in the water/gas shift reactor. According the process as disclosed herein, both gaseous hydrogen and carbon monoxide are required for the production of dimethyl ether as an intermediate step in the production of gasoline.

A function of the water/gas shift reactor 42 is to convert at least a portion of carbon monoxide and hydrogen gas to carbon dioxide so as to increase the $H_2$:CO ratio within a continuous second cleaned synthesis gas stream 78. The residence time of the carbon monoxide and hydrogen gas in the water/gas shift reactor 42 is sufficient for complete conversion; however other retention times may be realized in optimization of the disclosed process respective to individual process set-ups. The proper balancing of carbon monoxide and hydrogen gas for downstream dimethyl ether production and ultimately $C_5$ to $C_{12}$ hydrocarbon 85 productions is a function of the water/gas shift reactor 42. Additionally, it will be appreciated that the minimization of carbon formation within the water/gas shift 42 reactor is necessary in order to maximize the effective life of the catalyst material. Reactor operating conditions of temperature, pressure, and steam content all affect carbon formation. In addition, the content of methane produced as a by-product in the water/gas shift reactor 42 is monitored to determine the efficiency of the reactor 42.

Although the reactions inside the water/gas shift reactor 42 may vary with manufacture's suggested guidelines, the reaction conditions are preferably from about 200° C. to about 300° C. and at a pressure of from about 40 psi to about 500 psi (about 279 kPa to about 3496 kPa). In the case of a high temperature reaction, greater than 350° C., pressure is adjusted to maintain the space velocity of 8,000 standard cubic feet per second (scfs), whereas the low temperature reaction, >200° C., the pressure is adjusted to maintain the space velocity of 6,000 scfs.

The carbon monoxide, carbon dioxide, and hydrogen exit the water/gas shift reactor 42 and are introduced to another reactor 46 as shown in FIG. 1, wherein the carbon dioxide is selectively removed. The carbon dioxide is preferably removed from the second cleaned synthesis gas stream 78 in the reactor 46 by Selexol™ produced by Dow Chemicals, which is an acid gas removal solvent capable of separating carbon dioxide feed synthesis gas streams under pressure. However, it will be appreciated that any suitable method to remove carbon dioxide from a synthesis gas stream may be used for the purposes of the currently outlined process. For example, amine-based acid gas removal solvents that rely on a chemical reaction with the acid gases to remove carbon dioxide may be used and/or the Rectisol™ process may be used in alternative embodiments.

In the reactor 46 wherein carbon dioxide is selectively removed, at least 50% of the carbon dioxide is removed from the second cleaned synthesis gas stream 78. Preferably, between from about 50% to about 100% of the carbon dioxide is the removed from the second cleaned synthesis gas stream 78 at this point. Even more preferably between from about 80% to about 100% of the carbon dioxide is removed from the second cleaned synthesis gas stream 78. Optimally, in the reactor 46, at least about 98% of the carbon dioxide is removed from the second cleaned synthesis gas stream 78 at this point.

As is shown in FIG. 1, the second cleaned synthesis gas stream 78, now substantially devoid of carbon dioxide, and thus composed of primarily carbon monoxide and hydrogen, exits the reactor 46 and is introduced to a second compressor 48. In the second compressor 48, the second cleaned synthesis gas stream 78, composed primarily of carbon monoxide and hydrogen, is compressed to at least 5.5 MPa and moved to a slurry reactor 50 to be catalytically converted to produce a first mixture 80 substantially comprising dimethyl ether (DME) and to a lesser extent, un-reacted carbon monoxide, and hydrogen. In the slurry reactor 50, water and methanol may also be produced. The catalytic reaction in the slurry reactor 50 converts the second cleaned synthesis gas stream 78 to the first mixture 80, using a base metal catalyst. Preferred base metal catalysts used in the catalytic slurry reactor 50 are Ni, Cu, Zn and Fe, however any suitable base metal catalyst may be used. Preferably, particles of copper and zinc oxide on alumina particles are used in the catalytic slurry reactor 50 for the formation of the DME in the first mixture 80. Additionally, in the slurry reactor 50 the reaction is to be carried out at from about 225° C. to about 300° C. Preferably, the catalytic reaction in the slurry reactor 50 is carried out at a temperature of from about 250° C. to about 270° C. Optimally, the catalytic reaction in the slurry reactor 50 is carried out at a temperature of about 260° C. Furthermore, the catalytic reaction in the slurry reactor 50 is carried out at a pressure of from about 2.5 MPa to about 7.5 MPa. Preferably, the pressure of the catalytic reaction in the slurry reactor 50 to produce the first mixture 80 as noted above is between from about 4.5 MPa to about 6.5 MPa. Optimally, the pressure of the catalytic reaction in the slurry reactor 50 is about 5.5 MPa.

Inside the slurry reactor 50, the follow reactions take places substantially simultaneously to produce dimethyl ether, and thus the first mixture 80. Methanol and Carbon dioxide are also produce in the slurry reactor 50 as is shown in reactions 3 and 5 respectively below. The methanol of reaction 3 however is substantially converted to dimethyl ether in reaction 4 as shown.

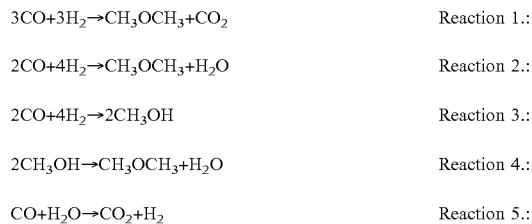

With reference to FIG. 1, the first mixture 80, exits the catalytic slurry reactor 50. The first mixture 80 as it exits the catalytic slurry reactor 50 comprises primarily dimethyl ether and to a lesser extent methanol, un-reacted carbon monoxide, formed carbon dioxide, un-reacted hydrogen and water. The first mixture 80 is then introduced into a gas/liquid separator 52. The gas/liquid separator 52 separates the gases and liquids from the first mixture 80, in a series of separation steps. In certain embodiments, following the gas/liquid separation in the gas/liquid separator 52, resulting methanol 54 from the slurry reactor 50 is recycled back through to the slurry reactor to be re-reacted to form dimethyl ether. Also, in certain embodiments, carbon monoxide, carbon dioxide and hydrogen, having been separated from the first mixture 80 in the gas/liquid separator 52 as gases 56, are recycled back through the water/gas shift reactor 42 to be reprocessed and joined back into the second clean synthesis gas stream 78 as is noted in FIG. 1. Water is also separated from the first mixture 80 in the gas/liquid separator 52 and removed.

As shown in FIG. 1, DME is selectively collected from the gas/liquid separator 52 and introduced to an on-line gasoline reactor 58. Dependent on the capacity of the on-line gasoline reactor 58 and the volume of DME produced in the catalytic slurry reactor 50 and subsequently separated from the first mixture 80 in the gas/liquid separator 52, more than one on-line gasoline reactor 58 as shown is FIG. 1 may be desirable in certain embodiments. To represent the more than one on-line gasoline reactor 58, a separate off-line gasoline reactor 44a is shown in FIG. 1.

In the on-line gasoline reactor 58, DME is catalytically converted to alkanes and non-oxygenated hydrocarbons using a zeolite shape-selective catalyst. Preferably, the zeolite catalyst used in the on-line gasoline reactor 58 is a 10-pore zeolite, with a high ratio of silica to alumina, ranging from about 298:1 to about 2000:1. The reaction conditions in the on-line gasoline reactor 58 for the zeolite catalytic production of alkanes and non-oxygenated hydrocarbons from DME are preferably from about 350° C. to about 450° C. and at a pressure of preferably from about 20 psi to about 50 psi (about 140 kPa to about 350 kPa). More preferably the zeolite catalytic reaction conditions in the on-line gasoline reactor 58 are from about 370° C. to about 390° C. and at a pressure of preferably from about 25 psi to about 45 psi (about 175 kPa to about 315 kPa). Optimally, the zeolite catalytic reaction conditions in the on-line gasoline reactor 58 are about 380° C. and at a pressure of about 30 psi (about 210 kPa).

Inside the gasoline reactor 58 $C_5$ to $C_{12}$ hydrocarbons are produced generally according to Reaction 6 as noted below.

$$CH_3OCH_3 \rightarrow C_nH_{2n+2} + C_nH_{2n} + C_nH_{2n-6} \qquad \text{Reaction 6.}$$

A second mixture 82, comprising primarily alkanes and non-oxygenated hydrocarbons, exits the on-line gasoline reactor 58 and is introduced into a distillation reactor 60.

Also exiting the on-line gasoline reactor 58, to a lesser extent, is un-reacted DME in the second mixture 82. In certain embodiments, DME in the second mixture 82 is separated from the alkanes and non-oxygenated hydrocarbons in the distillation reactor 60. However, it should be noted that DME, at this stage, can be separated from the alkanes and non-oxygenated hydrocarbons by any suitable method, for example a molecular sieve apparatus may optionally be utilized in a separate reactor (not shown). The DME separated from the second mixture 82 may optionally be recycled back to the on-line gasoline reactor 58 to be incorporated back into the first mixture 80 and re-processed in the on-line gasoline reactor 58 via the zeolite shape-selective catalyst as is shown at 119.

$C_5$ to $C_{12}$ alkanes 85 are selectively separated from the second mixture 82 in the distillation reactor 60 by distillation. Other compounds may be present in the second mixture 82, such as for example, alkenes, alkynes, aromatic compounds and napthalenes. The alkenes, alkynes, aromatic compounds and napthalenes may also be obtained from the second mixture for use in a $C_5$ to $C_{12}$ hydrocarbon fuel 85. However, it should be appreciated any suitable method for obtaining $C_5$ to $C_{12}$ alkanes 85 from the second mixture 82 may be used. Also, $C_3$ to $C_4$ alkanes and alkanes 72 having a carbon skeleton of greater that $C_{13}$ are separated via distillation in the distillation reactor 60. In certain embodiments, the $C_3$ to $C_4$ alkanes and alkanes 72 having a carbon skeleton of greater that $C_{13}$ are collected from the distillation reactor 60 and recycled back to the auto thermal reformer 40 to join in the second cleaned synthesis gas stream 78 and be re-processed (not shown). Additionally, water is separated from the second mixture 82 in the distillation reactor 60. The $C_5$ to $C_{12}$ alkanes 85 are collected from the distillation reactor 60 and stored in a gasoline storage container 62 as is shown in FIG. 1.

In the catalytic slurry reactor 50, the catalytic conversion of the carbon monoxide and hydrogen to the DME is an exothermic reaction and as such heat is generated. Nearly 700 kJ of energy per DME-mol is generated. With particular reference to FIG. 1. at 84, the change in the heat is noted for the catalytic slurry reactor 50 step of the process. The overall process described herein is energy dependant; however it is exo-energetic. The heat generated by the exothermic reaction in the catalytic slurry reactor 50, in certain embodiments may optionally be used to heat a stream boiler 64 or other similar pressure generating device, to produce steam or other turbine powering means suitable to drive a turbine 66 to produce electrical power 68. The generated electrical power 68 may optionally be supplied to an electrical grid network for consumer use and/or be used to power the process of the present disclosure at power-requiring steps or reactions. Also, the heat generated via the exothermic reaction in the catalytic slurry reactor 50 may be used to provide heat to the steps of the currently disclosed process where the process requires heat or to stimulate endothermic reactions of the currently disclosed process. Likewise, the catalytic reaction which takes place in the on-line gasoline generator 58 is exothermic. The heat and energy generated from the on-line gasoline reactor 58 may similarly be used as aforementioned with respect to the exothermic reaction of the catalytic slurry reactor 50.

EXAMPLES

For the purposes of further clarity of the currently disclosed process, the following non-limiting examples are provided. The examples disclosed herein should not be taken to be restrictive of the currently disclosed technology, nor should they be taken to confine the currently disclosed technology to the specific parameters as disclosed therein. The following examples make reference to figures and the steps and devices comprised therein.

Example 1

The primary elements of the process for producing liquid and gaseous hydrocarbons, plus water, of the present invention is shown generally at 10 in the block diagram of FIG. 1. In this diagram, solid organic material such as wood is utilized as organic feedstock 12. In the following description, variations on the process are included.

Organic feedstock 12 is prepared to enter the heating device also herein referred to as the gasifier 20. The organize feedstock 12 can be comprised of any or a combination of vegetative material, components of household garbage, man-made organic compounds such as plastic or rubber or a described above. In a preferred embodiment, wood chips are prepared as described with reference to FIG. 1, by reducing in particle size 14 and drying 16 to suit uniform feeding and heating. Following preparation, the wood chips 12 are then fed into the heating device 20. The heating device 20, for example, may be, but not limited to, a fluidized bed gasifier, a circulating bed gasifier, an induction furnace, a rotary kiln, or a plasma reactor. The heating device 20 is selected efficiently partially to convert the organic feedstock into a synthesis gas 74 comprising primarily carbon monoxide and hydrogen, herein referred in the alternative to as "syngas". Owing to the inefficiencies of most heating devices or gasifiers 20, some hydrocarbon gases such as, for example, alkanes, alkenes or alkynes (such as, for example, methane) may also be formed in the heating process, as well as carbon dioxide. Additionally, there may also be other components in the syngas stream 74, such as particulate matter comprised of carbon and ash. Furthermore, nitrogen compounds, chlorine, sulfur, etc, may also be present dependent on the original chemical composition of the organic feedstock 12. In the embodiment of the present example, a heating device or gasifier 20 is chosen to substantially gasify wood chips 12.

In the embodiment of the present example, steam 114 is optionally fed into the gasifier 20 to aid in fluidizing the bed for uniformity, and also to promote a water-shift reaction and increase the volume of hydrogen generated.

In the embodiment of the present example, oxygen is also fed into the gasifier 20, as is shown in FIG. 1 at the gasifier 20 and the oxygen generator 22, at substoichiometric conditions to promote partial combustion of the organic feedstock 12. Also, in the embodiments, oxygen can be derived from the atmosphere using a molecular sieve device (not shown), in which case nitrogen separated from the gases may be safely vented from the process. In other cases, the oxygen may be supplied through separate means, such as an oxygen generator 22 or other suitable methods of supplying oxygen. The volume of oxygen supplied to the gasifier 20 is a calculated amount which is determined and selected to partially combust the inputted organic feedstock 12.

The heating device 20 may be heated to the appropriate temperature to efficiently gasify the organic feedstock 12. This temperature is determined on the basis of the input organic feedstock 12, for example, in the case of the wood chips of the present example, the device is to be heated to approximately 800° C. In the embodiment of the present example, the heating device 20 is a directly-fired fluidized bed gasifier, where the input organic feedstock 12 is partially combusted such that no extraneous heat is required to maintain the reaction since once the reaction in the heating device 20 is started; heat is generated from the combustion reaction to propagate further combustion. However, if required, the heating device 20 may, among other suitable means be an externally heated (for example, induction heating and/or a rotary kiln) and/or the heating device 20 may utilize hot bed material (for example, a circulating bed) or direct energy transfer (for example, plasma) to gasify the organic feedstock 12. Depending on the organic feedstock utilized, an appropriate device, best suited to produce high quality synthesis gas 74 from the organic feedstock is chosen.

The synthesis gas 74 emerging from the heating device 20 is then cleaned in a particle cleaning device 24 to remove any particulate matter. The cleaning device 24, for example, may accomplish cleaning of the syngas 74 by the use of cyclones, also known as cyclone cleaners and/or other suitable equipment such as bag houses or filters. In the case of the present example, cyclones are utilized and the particulate matter 117 is removed from the syngas 74 to produce a first cleaned synthesis gas stream 76 as is shown in FIG. 1.

The first cleaned syngas stream 76 is then scrubbed using a venturi scrubber 26 arrangement in which the scrubbing solution used contains, in the present example, alkaline chemicals, such as NaOH or KOH to remove any chlorine or other acids which may be present in the first cleaned synthesis gas 76. The condensing effect of this liquid scrubbing also cools the gases, and any light oils or tars 28, which are contained in the first cleaned synthesis gas 76, are thus condensed out of the first cleaned synthesis gas stream 76. The light oils and tar 28 are borne with the alkaline water solution of the venturi scrubber 26 and removed from the first cleaned synthesis gas 76. It should be noted that dependent upon the composition of the organic feedstock 12 and the type of heating device 20, the venturi scrubbing step 26 may not be required, or the scrubbing solution may be necessarily different in composition depending on the chemicals present in the first cleaned synthesis gas stream 76, which must be substantially removed. The required purity of the first cleaned syngas stream 76 will dictate the equipment and scrubbing compositions required in the venturi scrubber 26.

In the present example, the water/light oils and tars mixture 28 from the venturi scrubber 26 are sent to an oil/water separator where the water is separated from the oils or tar, not shown in FIG. 1. The water is then removed from the system and the tars and/or oils 28 are returned to the heating device 20 for re-processing.

The first cleaned synthesis gas stream 76 is then compressed in a compressor 30 and aids in water 32 removal from the first cleaned synthesis gas stream 76 and forwarded in the process of the present example to a guard bed 34, or series of guard beds 34, as is shown in FIG. 1, to remove further contaminants 36, such as, for example sulfur, from the first cleaned synthesis gas stream 76 which may oxidize the catalysts in the downstream process, thus conditioning and further cleaning the first cleaned synthesis gas stream. It should be noted that the type and use of the aforementioned guard bed(s) 34 is to be dictated by the chemical composition of the organic feedstock 12 from which the synthesis gas 74 is produced. The first cleaned synthesis gas stream 78, now emerging from the guard bed(s) 34 as a second cleaned synthesis 78 is forwarded to an alkane/hydrocarbon or gas separator 38 to separate any hydrocarbon gases such as alkanes, alkenes or alkynes which may be present in the second cleaned synthesis gas 78 at this stage in the process. The volume and species of hydrocarbon gases such as alkanes, alkenes or alkynes present are determined by the heating device 20 and its relative efficiency in regards to the extent to which the organic feedstock 12 is partially oxidized. The hydrocarbon gases such as alkanes, alkenes or alkynes from the alkane/hydrocarbon or gas separator 38 are forwarded to a reformer 40 as shown in FIG. 1. The remainder of the second cleaned synthesis gas stream 78, comprised of carbon monoxide, hydrogen and carbon dioxide is forwarded directly to a water shift reactor 42.

The purpose of the reformer 40, as discussed above, is to convert any hydrocarbon gases such as alkanes, alkenes or alkynes, such as, for example, methane, which have formed in the heating device 20 or have formed in later process steps, into additional first cleaned synthesis gas 76, thereby utilizing as much carbon from the organic feedstock 12 as possible. The type of reformer selected in this step is determined by the volume of hydrocarbon gases such as alkanes, alkenes or alkynes present in the gases. In the embodiment of the present example, an autothermal reformer (ATR) 40 is utilized, and oxygen from an oxygen generator 22 and/or other suitable means of introducing oxygen, is fed into the auto thermal reformer 40. The ATR 40 of the present example utilizes a nickel catalyst to form CO and $H_2$ in a ratio ranging from about 1:1 to about 1:2. It is preferred in the present example that the ratio of CO to $H_2$ be approximately 1:2. Furthermore, in the present example, steam may also be required in this step, (not shown in FIG. 1), which can be supplied directly or optionally from elsewhere in the process, such as, for example, from the steam boiler 64. Other carbon-based gases, for example those removed in the final distillation column 60 may also, optionally be fed into this reformer 40 for processing to carbon monoxide, carbon dioxide and hydrogen.

It should be understood, that the second cleaned syngas stream 78 emerging from the reformer 40 will likely contain a small amount of hydrocarbon gases such as alkanes, alkenes or alkynes, owing to the fact that no reformer is 100% efficient. The hydrocarbon gases such as alkanes, alkenes or alkynes emerging from the reformer 40 in the present example may optionally be directed to the alkane/hydrocarbon or gas separator 38 where the hydrocarbon gases such as alkanes, alkenes or alkynes are separated (not shown). These hydrocarbon gases such as alkanes, alkenes or alkynes may then be re-processed back through the reformer 40 to produce carbon monoxide, carbon dioxide and hydrogen to be added back into the second cleaned synthesis gas stream 78 and processed at the next step of the process.

The exiting second cleaned synthesis gas stream 78, comprising substantially carbon monoxide, carbon dioxide and hydrogen from the alkane/hydrocarbon or gas separator 38 and/or the reformer 40 are forwarded to a water/gas shift reactor 42. In the water/gas shift reactor 42 under heat of from about 200° C. to about 300° C. and pressure of from about 40 psi to about 500 psi (about 279 kPa to about 3496 kPa), and in the presence of a nickel catalyst and steam convert a portion of the carbon monoxide in the second cleaned syngas stream 78 at this point in the process into carbon dioxide, as discussed above. In the present example embodiment, this step is utilized to adjust the $CO:H_2$ ratio in favor of the chemical reactions which follow in subsequent steps in the process. Although the ratio of $CO:H_2$ may be variable, the preferred ratio of $CO:H_2$ exiting the water/gas shift reactor 42 is from about 1:1 to about 1:2.

The second cleaned syngas stream 78 emerging from the water/shift reactor 42 is then compressed (not shown) from 200 to 2000 kPa before entering the carbon dioxide removal system 46. This system may be a methanol-type solvent removal process, or an amine solution removal process; however, in the present example embodiment, the Selexol™ process specified by Dow Chemical is utilized, which removes most of the $CO_2$ from the second synthesis gas stream 78 at this point. As an alternative, the Rectisol™ process may also utilized at this point to remove $CO_2$ from the second cleaned synthesis gas 78. Furthermore, $CO_2$ may be substantially removed from the second cleaned synthesis gas stream 78 in the carbon dioxide removal system 46 by any acceptable combination of the aforementioned $CO_2$ removal processes. The $CO_2$ thus removed from the second cleaned synthesis gas 78 may either be vented or collected, and may be utilized elsewhere in the process, for example, as an inert gas blanket in the surge bin 18.

The second cleaned synthesis gas stream 78 from carbon dioxide removal system 46, the $CO_2$ removal step, is then forwarded to a catalytic reactor 48 to be substantially converted to dimethyl ether. The catalytic slurry reactor 48 utilizes a base metal catalyst, for example a copper oxide, zinc oxide on alumina at a temperature of about 300° C. and a pressure of about 2834 kPa to convert the CO and $H_2$ into dimethyl ether ($C_2H_6O$). It should be noted that although in the present example, a base metal catalyst is preferred, several catalysts and methods can be utilized for this reaction. In the present example embodiment, a catalytic slurry reactor 48 is employed, and the catalyst conversion rate on the first pass through the reactor is about 50% using a base metal catalyst and the aforementioned reaction conditions.

The gases emerging from the slurry reactor 48 form a first mixture 80, comprising carbon monoxide, carbon dioxide, hydrogen, water, methanol and dimethyl ether, which are separated in a liquid/gas separation system 52. In this separation, happening in the liquid/gas separation system 52, the un-reacted gases, for example carbon monoxide, carbon dioxide and hydrogen are recycled back to the shift reactor 54 and methanol which is recycled back to the slurry reactor 48 to be re-reacted to form dimethyl ether. Water is removed by the separation system 52 and can optionally be utilized elsewhere in the process or discarded.

Dimethyl ether emerging from the liquid gas separation system 52 is forwarded to an on-line gasoline reactor 58 to form non-oxygenated hydrocarbons. In the embodiment of the present example, a modified zeolite-shaped catalyst is utilized in a reactor operating at a temperature of about 450° C. and at a pressure of about 200 kPa to convert the dimethyl ether into a mixture of non-oxygenated hydrocarbons. The reaction conditions provided preferably produce non-oxygenated hydrocarbons having a carbon skeleton ranging in size from $C_5$ to $C_{12}$, among other compounds, thus forming a second mixture 82.

The second mixture 82 emerging from the on-line gasoline reactor 58 is forwarded to a distillation column 60. The liquids which condense are then separated by the column 60 into water and hydrocarbons, and gases, such as un-reacted butane or propane from the on-line gasoline reactor 58 which emerges from the top of the column. Hydrocarbons gases having a carbon skeleton of $C_4$ or less 72 are sent back to the reformer 40 to be reprocessed. Non-oxygenated hydrocarbons having a carbon skeleton of $C_5$ to $C_{12}$ 85 are forwarded to a gasoline storage vessel 62 where they are collected.

The hydrocarbons having a carbon skeleton of $C_4$ or less and $C_{13}$ or greater 72 are recycled back to the reformer 40 to be converted into carbon monoxide, hydrogen and carbon dioxide and join into the second cleaned synthesis gas stream 78 as they emerge from the reformer 40. The hydrocarbon products having a carbon skeleton of $C_5$ to $C_{12}$ alkanes 85 are then removed from the process and sent to storage 62.

Example 2

Figure 2:
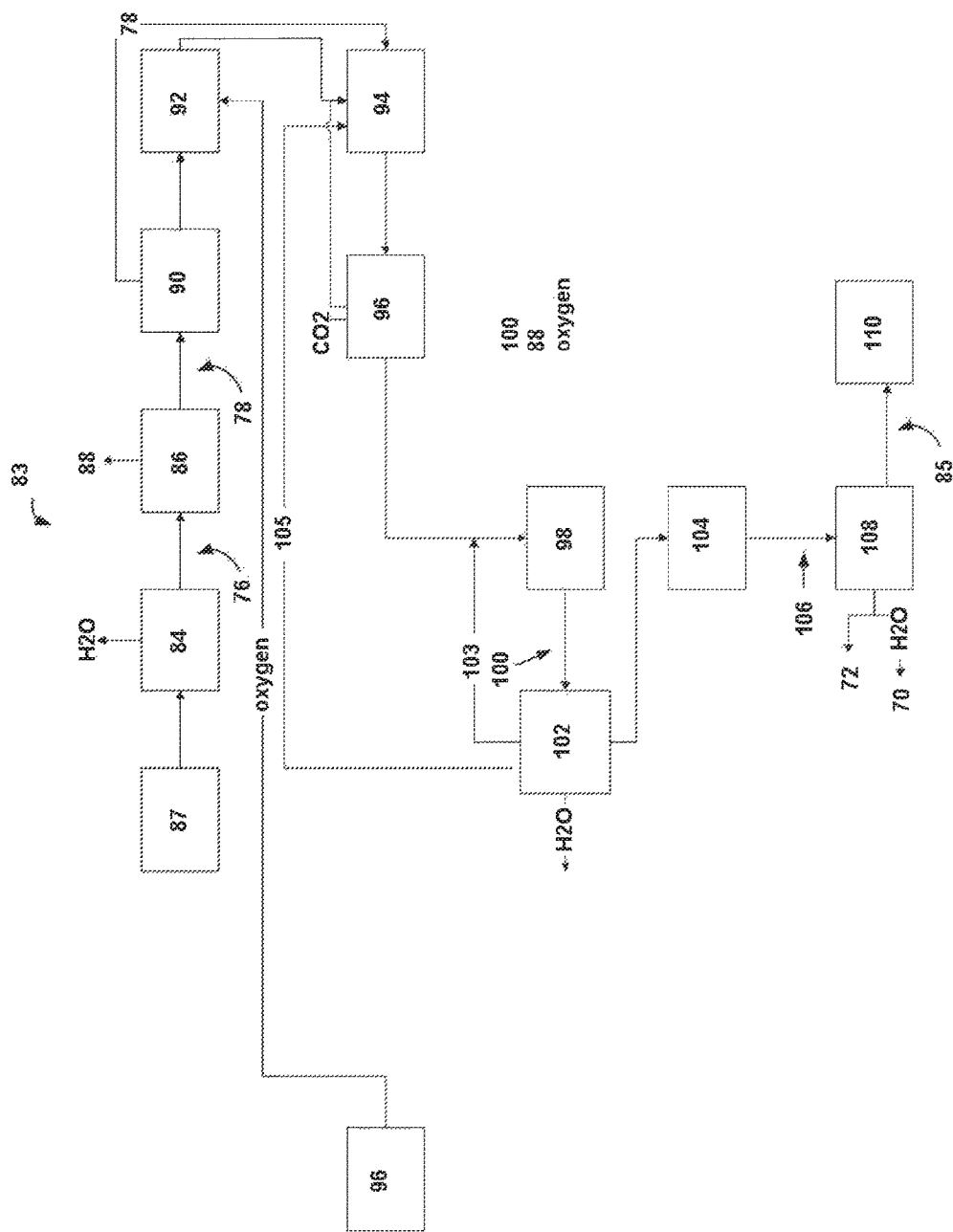
FIG. 2 is a schematic block diagrammatical representation of an embodiment of the process of the present invention starting from gaseous organic feedstock, relating to Example 2 below.

In an alternative embodiment disclosed in the present example, generally shown in FIG. 2 at 83, a gaseous organic feedstock 87 is utilized. For the purposes of the present example, the gas may be a single compound or a mixture of carbon-based organic gases. It should be understood that non-carbon-based gases and compounds may also be present in the gaseous organic feedstock 87 of the present example. For example, the gases referred to in the present example may be those resulting from the anaerobic digestion of manures or municipal sewage sludge, or landfill gas, which are likely to be or contain methane and carbon dioxide among other present compounds. By way of example of a single compound is propane, which may be the by-product of another process, can be utilized in an embodiment of the present example. The aforementioned gases are by way of examples; one skilled in the art will appreciate that many different possibilities exist for gaseous organic feedstock 87, which may arise as by-products from other processes and are unwanted or have no commercial value but are suitable for use in the currently described process.

Although not shown in the figures, a cleaning step may be comprised of a scrubbing step to remove contaminants, or simply to remove extraneous particulate matter from the supplied gaseous organic feedstock 87. For example, cyclone-type particle removal systems and venturi scrubbing systems using an alkaline water solution, or other suitable means may be used to clean the gaseous organic feedstock 87 prior to introduction into the process of the present example, thus comprising a cleaned synthesis gas stream.

With reference to FIG. 2, the optionally cleaned synthesis gas stream is then compressed in a compressor 84 which aids in water removal from the cleaned synthesis gas steam, thus producing a first cleaned synthesis gas stream 76. The first cleaned synthesis gas stream 76 is then forwarded in the process of the present example to a guard bed 86, or series of guard beds 86, as is shown in FIG. 2, to remove further contaminants 88 such as, for example sulfur, which may oxidize the catalysts in the downstream process, thus conditioning and further cleaning the first cleaned synthesis gas stream 76 to produce a second cleaned synthesis gas stream 78. It should be noted that the type and use of the aforementioned guard bed(s) 86 is to be dictated by the chemical composition of the gaseous organic feedstock 87 from which the first cleaned synthesis gas stream 76 is produced. The cleaned synthesis gas stream 76, now emerging from the guard bed(s) 86 as a second cleaned synthesis gas stream 78 is forwarded to an alkane/hydrocarbon or gas separator 90 to separate any hydrocarbon gases such as alkanes, alkenes or alkynes which may be present in the second cleaned synthesis gas 78 at this stage in the process. The volume and species of hydrocarbon gases such as alkanes, alkenes or alkynes present are determined by the initial composition of the gaseous organic feedstock 87. The hydrocarbon gases such as alkanes, alkenes or alkynes from the alkane/hydrocarbon or gas separator 90 are forwarded to a reformer 92 as shown in FIG. 2. The remainder of the second cleaned synthesis gas stream 78, comprised of carbon monoxide, hydrogen and carbon dioxide is forwarded directly to a water/gas shift reactor 94.

The purpose of the reformer 92 is to convert any hydrocarbon gases such as alkanes, alkenes or alkynes, such as, for example, methane, which may have formed in the preceding processing steps or have been present in the gaseous organic feedstock 87, into additional first cleaned synthesis gas 76, thereby utilizing as much carbon from the gaseous organic feedstock 87 as possible. The reactions and requirements of a reformer are discussed above with respect to the alkane reformer reactor 42 of FIG. 1. A similar reformer to that of FIG. 1 is suitable for use in the current example. The type of reformer selected in this step is determined by the volume of hydrocarbon gases such as alkanes, alkenes or alkynes present in the gases. In the embodiment of the present example, an autothermal reformer (ATR) 92 is utilized, and oxygen from an oxygen generator 96 and/or other suitable means of introducing, is fed into the auto thermal reformer 92. The ATR 92 of the present example utilizes a nickel catalyst to form CO and $H_2$ in a ratio ranging from about 1:1 to about 1:2. It is preferred in the present example that the ratio of CO to $H_2$ be approximately 1:2. Furthermore, in the present example, steam may also be required in this step, (not shown in the process of FIG. 2), which can be supplied directly or optionally from elsewhere in the process. Other carbon-based gases may also, optionally be fed into this reformer 92 for processing to carbon monoxide, carbon dioxide and hydrogen.

It should be understood, that the second cleaned syngas stream 78 emerging from the reformer 92 will likely contain a small amount of hydrocarbon gases such as alkanes, alkenes or alkynes, owing to the fact that no reformer is 100% efficient. The hydrocarbon gases such as alkanes, alkenes or alkynes emerging from the reformer 92 in the present example may optionally be directed to the alkane/hydrocarbon or gas separator 90 where the hydrocarbon gases such as alkanes, alkenes or alkynes are separated (not shown). These hydrocarbon gases such as alkanes, alkenes or alkynes may then be re-processed back through the reformer 92 to produce carbon monoxide, carbon dioxide and hydrogen to be added back into the second cleaned synthesis gas stream 78 and processed at the next step in the process.

The exiting second cleaned synthesis gas stream 78, comprising substantially carbon monoxide, carbon dioxide and hydrogen from the alkane/hydrocarbon or gas separator 90 and/or the reformer 92 is forwarded to a water/gas shift reactor 94. In the water/gas shift reactor 94 under heat and pressure the reaction conditions are preferably from about 200° C. to about 350° C. and at a pressure of from about 40 psi to about 500 psi (about 279 kPa to about 3496 kPa). In the case of a high temperature reaction, greater than about 350° C., pressure is adjusted to maintain the space velocity of 8,000 scfs, whereas the low temperature reaction, greater that about 200° C., the pressure is adjusted to maintain the space velocity of 6,000 scfs, and in the presence of a nickel catalyst and steam convert a portion of the carbon monoxide in the second cleaned syngas stream 78 at this point in the process into carbon dioxide. In the present example embodiment, this step is utilized to adjust the $CO:H_2$ ratio in favor of the chemical reactions which follow in subsequent steps in the process. Although the ratio of $CO:H_2$ may be variable, the preferred ratio of $CO:H_2$ exiting the water/gas shift reactor is from about 1:1 to about 1:2.

The second cleaned syngas stream 78 emerging from the water/shift reactor 94 is then compressed (not shown) from 200 to 2000 kPa before entering a carbon dioxide removal system 96. This system may be a methanol-type solvent removal process, or an amine solution removal process however, in the present example embodiment, the Selexol™ process specified by Dow Chemical is utilized, which removes most of the $CO_2$ from the second synthesis gas stream 78 at this point. As an alternative, the Rectisol™ process may also utilized at this point to remove $CO_2$ from the second cleaned synthesis gas 78. Furthermore, $CO_2$ may be substantially removed from the second cleaned synthesis gas in the carbon dioxide removal system 96 by any acceptable combination of the aforementioned $CO_2$ removal processes. The $CO_2$ thus removed from the second cleaned synthesis gas 78 may either be vented or collected.

The second cleaned synthesis gas stream 78 exiting from the carbon dioxide removal system 96, the $CO_2$ removal step, is then forwarded to a catalytic slurry reactor 98 to be substantially converted to dimethyl ether. The slurry reactor 98 utilizes a base metal catalyst at a temperature of about 260° C. and a pressure of about 5500 kPa to convert the CO and $H_2$ into dimethyl ether ($C_2H_6O$). It should be noted that although in the present example, a base metal catalyst is preferred, several catalysts and methods can be utilized for this reaction. In the present example embodiment, a catalytic slurry reactor 98 is employed, and the catalyst conversion rate on the first pass through the catalytic slurry reactor 98 is about 50% using a base metal catalyst and the aforementioned reaction conditions. The gases emerging from the catalytic slurry reactor 98 form a first mixture 100, comprising carbon monoxide, hydrogen, water, methanol and dimethyl ether, which are separated in a liquid/gas separation system 102. In this separation, happening in the liquid/gas separation system 102, the un-reacted carbon monoxide, carbon dioxide and hydrogen gases 105 and a methanol 103 may be recycled back to the slurry reactor 98 to be re-reacted to form dimethyl ether (not shown). Water is removed from the separation system 102 and can optionally be utilized elsewhere in the process or discarded.

Dimethyl ether emerging from the liquid gas separation system 102 is forwarded to an on-line gasoline reactor 104 to form non-oxygenated hydrocarbons. In the embodiment of the present embodiment, a modified zeolite-shaped catalyst is utilized in the on-line gasoline reactor 104 operating at a temperature of about 450° C. and at a pressure of about 200 kPa to convert the dimethyl ether into a mixture of non-oxygenated hydrocarbons. The reaction conditions provided preferably produce non-oxygenated hydrocarbon having a carbon skeleton ranging in size from $C_5$ to $C_{12}$, among other compounds, thus forming a second mixture 106.

The second mixture 106 emerging from the on-line gasoline reactor 104 is forwarded to a distillation column 108. The liquids which condense are then separated by the column 108 into water and hydrocarbons, and gases, such as un-reacted dimethyl ether from the on-line gasoline reactor 104 which emerges from the top of the column. Hydrocarbons having a carbon skeleton of $C_4$ or less 72 are sent back to the reformer 92 to be reprocessed. Non-oxygenated hydrocarbons having a carbon skeleton of $C_5$ to $C_{12}$ 85 are forwarded to a gasoline storage vessel 110 where they are collected.

The hydrocarbons having a carbon skeleton of $C_4$ or less and $C_{13}$ or greater 72 may be recycled back to the reformer 92 (not shown) to be converted into carbon monoxide, hydrogen and carbon dioxide and join into the second cleaned synthesis gas stream 78 as they emerge from the reformer 92. The hydrocarbon products having a carbon skeleton of $C_5$ to $C_{12}$ 85 are then removed from the process and sent to storage 110.

Example 3

Figure 3:
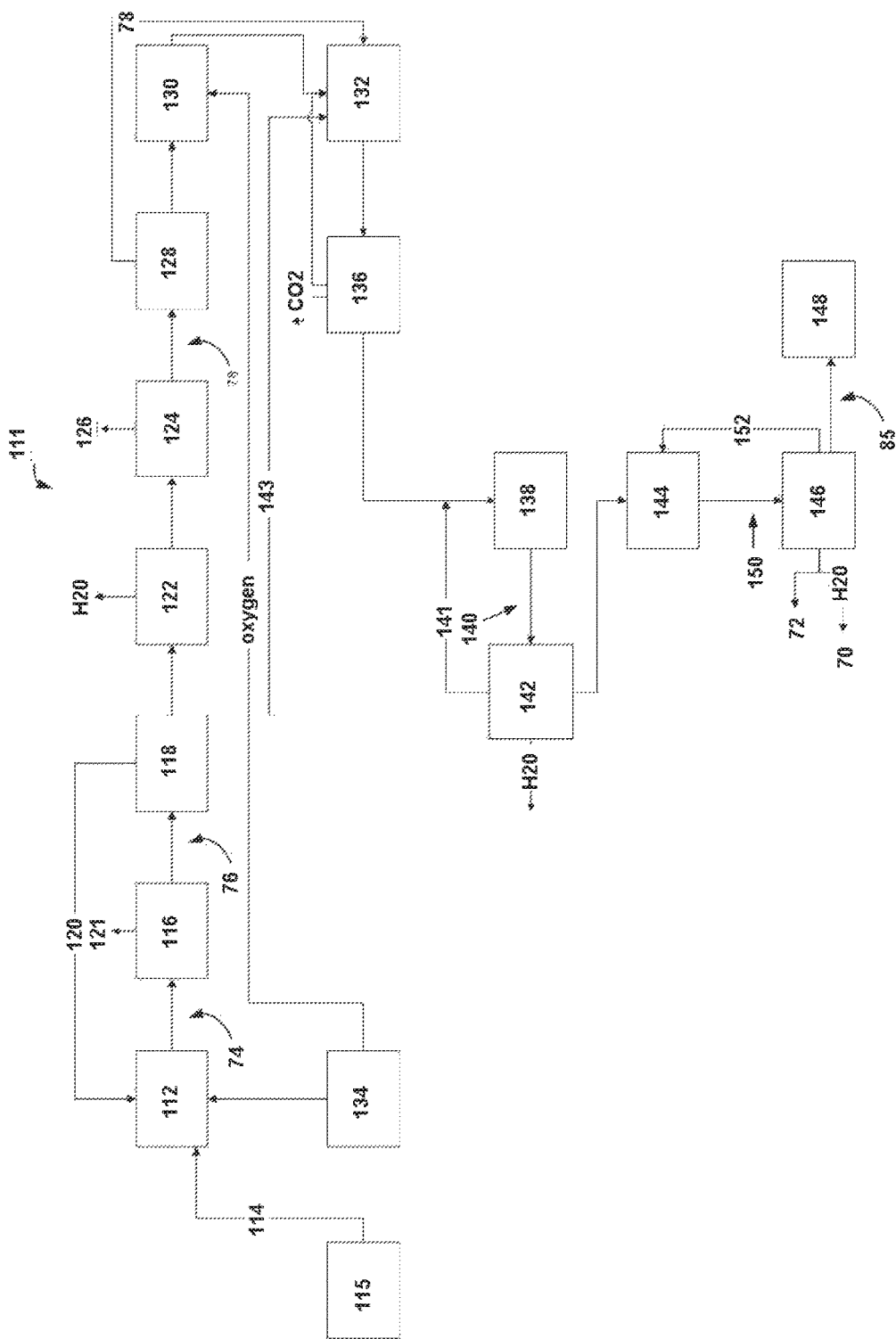
FIG. 3 is a schematic block diagrammatical representation of an embodiment of the process of the present invention starting from liquid organic feedstock, relating to Example 3 below.

In an alternative embodiment disclosed in the present example, generally shown in FIG. 3 at 111, liquid organic feedstock 115 is processed. For exemplary purposes, the liquid organic feedstock 115 may be bio-oil from the pyrolysis of cellulosic material. Alternatively, or in combination with the preceding, the liquid organic feedstock 115 may be black or green liquour resulting from the processing of wood for the preparation of pulp. As will be readily appreciated, the most appropriate liquid organic feedstocks 115 will be generally known as liquids which are "carbon-rich".

With reference to FIG. 3, the organic feedstock liquids 115 are fed into a heating device or gasifier 112. The heating device or gasifier 112 partially oxidizes liquid organic feedstock 115 to produce a synthesis gas 74 comprised primarily of carbon monoxide and hydrogen, but also may include carbon dioxide, hydrocarbons such as alkanes, alkenes or alkynes, suspended particulate matter, tars, or light oils among other compounds. The heating device or gasifier 112 may be selected from the group including but not limited to: fluid beds, resistance heaters, induction heaters, or plasma reactors or other types of heating devices or gasifiers which are suitable to carry out the currently disclosed process. Similar to Example 1, a process pertaining to solid organic feedstock, oxygen may be fed into the heating device 112, as is shown in FIG. 3 via an oxygen generator 134 to effect partial combustion of the liquid organic feedstock 115 to produce a syngas 74. In certain embodiments of the present example, steam may also be fed into the heating device 112, as is shown at 114, to facilitate the reaction.

Once the liquid organic feedstock 115 has been converted into a synthesis gas 74 in the gasifier 112, it is then cleaned of particulate matter in a cyclone-type cleaner 116 and any present solids 121 are removed to produce a first cleaned synthesis gas stream 76. It should be appreciated that the removal of solids 121 from the synthesis gas 74 by the cyclone cleaner 116 to produce a first cleaned synthesis gas stream 76 may be accomplished by the use of cyclones, also known as cyclone cleaners, as noted above, and/or other suitable equipment such as bag houses or filters. The first cleaned synthesis gas stream 76 is then further cleaned of contaminants as required, depending upon the composition of the original liquid organic feedstock 115.

The first cleaned syngas stream 76 is then, optionally scrubbed using a venturi scrubber 118 arrangement in which the scrubbing solution used contains, in the present example, alkaline chemicals, such as NaOH or KOH to remove any chlorine or other acids which may be present in the first cleaned synthesis gas 76. The condensing effect of this liquid scrubbing also cools the gases, and any light oils or tars 120 are removed as noted in FIG. 3, which are contained in the first cleaned synthesis gas 76, and thus condensed out of the first cleaned synthesis gas stream 76. The light oils and tars 120 are borne with the alkaline water solution of the venturi scrubber 118 and removed from the first cleaned synthesis gas 76. It should be noted that depending upon the composition of the liquid organic feedstock 115, the venturi scrubbing step 118 may not be required, or the scrubbing solution may be necessarily different in composition depending on the chemicals present in the first cleaned synthesis gas stream 76, which must be substantially removed. The required purity of the first cleaned syngas stream 76 will dictate the equipment and scrubbing compositions required in the venture scrubber 118.

In the present example, the water/light oils and tars mixture 120 from the venturi scrubber 118 are sent to an oil/water separator where the water is separated from the oils or tar 120, not shown in FIG. 3. The water is then removed from the system and the tars and/or oils 120 are returned to the heating device 112 for re-processing.

The first cleaned synthesis gas stream 76 is then compressed in a compressor 122 to aid in water removal from the first cleaned synthesis gas stream 76 and forwarded in the process of the present example to a guard bed 124, or series of guard beds 124, as is shown in FIG. 3, to remove further contaminants 126 such as, for example sulfur, which may oxidize the catalysts in the downstream process, thus conditioning and further cleaning the first cleaned synthesis gas stream 76 to produce a second cleaned synthesis gas stream 78. It should be noted that the type and use of the aforementioned guard bed(s) 124 is to be dictated by the chemical composition of the liquid organic feedstock 115 from which the synthesis gas 74 is produced. The first cleaned synthesis gas stream 76, now emerging from the guard bed(s) 124 as a second cleaned synthesis gas stream 78 is forwarded to an alkane/hydrocarbon or gas separator 128 to separate any hydrocarbon gases such as alkanes, alkenes or alkynes which may be present in the second cleaned synthesis gas stream 78 at this stage in the process. The volume and species of hydrocarbon gases such as alkanes, alkenes or alkynes present is determined by the heating device and its relative efficiency in regards to the extent to which the liquid organic feedstock 115 is partially oxidized. The hydrocarbon gases such as alkanes, alkenes or alkynes from the alkane/hydrocarbon or gas separator 128 are forwarded to a reformer 130 as shown in FIG. 3. The remainder of the second cleaned synthesis gas stream 78, comprised of carbon monoxide, hydrogen and carbon dioxide is forwarded to directly a water shift reactor 132.

The purpose of the reformer 132 is to convert any hydrocarbon gases such as alkanes, alkenes or alkynes, such as, for example, methane, which have formed in the heating device 112 or have formed in later process steps, into additional second cleaned synthesis gas 78, thereby utilizing as much carbon from the organic feedstock as possible. The reactions and requirements of a reformer are discussed above with respect to the alkane reformer reactor 42 of FIG. 1. A similar reformer to that of FIG. 1 is suitable for use in the current example. The type of reformer selected in this step is determined by the volume of hydrocarbon gases such as alkanes, alkenes or alkynes present in the gases. In the embodiment of the present example, an autothermal reformer (ATR) 130 is utilized, and oxygen from an oxygen generator 134 and/or other suitable means of introducing oxygen, is fed into the reformer 130. The ATR 130 of the present example utilizes a nickel catalyst to form CO and $H_2$ in a ratio ranging from about 1:1 to about 1:2. It is preferred in the present example that the ratio of CO to $H_2$ be approximately 1:2. Furthermore, in the present example, steam may also be required in this step, (not shown in FIG. 3), which can be supplied directly or optionally from elsewhere in the process. Other carbon-based gases may also optionally be fed into this reformer 130 for processing to carbon monoxide, carbon dioxide and hydrogen.

It should be understood, that the second cleaned syngas stream 78 emerging from the reformer 130 will likely contain a small amount of hydrocarbon gases such as alkanes, alkenes or alkynes, owing to the fact that no reformer is 100% efficient. The hydrocarbon gases such as alkanes, alkenes or alkynes emerging from the reformer 130 in the present example may optionally be directed to the alkane/hydrocarbon or gas separator 128 where the hydrocarbon gases such as alkanes, alkenes or alkynes are separated. These hydrocarbon gases such as alkanes, alkenes or alkynes may then be re-processed back through the reformer 130 to produce carbon monoxide, carbon dioxide and hydrogen to be added back into the second cleaned synthesis gas stream 78 and processed at the next step in the process.

The exiting second cleaned synthesis gas stream 78, comprising substantially carbon monoxide, carbon dioxide and hydrogen from the alkane/hydrocarbon or gas separator 128 and/or the reformer 130 are forwarded to a water/gas shift reactor 132. In the water/gas shift reactor 132 under heat and pressure the reaction conditions are preferably from about 200° C. to about 350° C. and at a pressure of from about 40 psi to about 500 psi (about 279 kPa to about 3496 kPa). In the case of a high temperature reaction, greater than about 350° C., pressure is adjusted to maintain the space velocity of 8,000 scfs, whereas the low temperature reaction, greater than about 200° C., the pressure is adjusted to maintain the space velocity of 6,000 scfs, and in the presence of a nickel catalyst and steam convert a portion of the carbon monoxide in the second cleaned syngas stream 78 at this point in the process into carbon dioxide and hydrogen. In the present example embodiment, this step is utilized to adjust the $CO:H_2$ ratio in favor of the chemical reactions which follow in subsequent steps in the process. Although the ratio of $CO:H_2$ may be variable, the preferred ratio of $CO:H_2$ exiting the water/gas shift reactor is from about 1:1 to about 1:2.

The second cleaned syngas stream 78 emerging from the water/shift reactor 132 is then compressed (not shown) from about 200 to about 2000 kPa before entering the carbon dioxide removal system shown at 136. This system may be a methanol-type solvent removal process, or an amine solution removal process. However, in the present example embodiment, the Selexol™ process specified by Dow Chemical is utilized, which removes most of the $CO_2$ from the second synthesis gas stream 78 at this point. As an alternative, the Rectisol™ process may also be utilized at this point to remove $CO_2$ from the second cleaned synthesis gas 78. Furthermore, $CO_2$ may be substantially removed from the second cleaned synthesis gas by the carbon dioxide removal system 136 by any acceptable combination of the aforementioned $CO_2$ removal processes. The $CO_2$ thus removed from the second cleaned synthesis gas 78 may either be vented or collected.

The second cleaned synthesis gas stream 78 exiting from the carbon dioxide removal system 136, the $CO_2$ removal step, is then forwarded to a catalytic slurry reactor 138 to be substantially converted to dimethyl ether. The catalytic slurry reactor 138 utilizes a base metal catalyst at a temperature of about 300° C. and a pressure of about 2834 kPa to convert the CO and $H_2$ into dimethyl ether ($C_2H_6O$). It should be noted that although in the present example, a base metal catalyst is preferred, several catalysts and methods can be utilized for this reaction. In the present example embodiment, a catalytic slurry reactor 138 is employed, and the catalyst conversion rate on the first pass through the catalytic slurry reactor is about 50% using a base metal catalyst and the aforementioned reaction conditions. The gases emerging from the catalytic slurry reactor 138 form a first mixture 140, comprising carbon monoxide, hydrogen, water, methanol and dimethyl ether, which are separated in a liquid/gas separation system 142. In this separation, happening in the liquid/gas separation system 142, the un-reacted gases carbon monoxide and hydrogen 143 at this stage are recycled back to the water/gas shift reactor 132 and methanol 141 is recycled back to the slurry reactor 138 to be re-reacted to form dimethyl ether. Water is removed from the separation system 142 and can optionally be utilized elsewhere in the process or discarded.

Dimethyl ether emerging from the liquid gas separation system 142 is forwarded to an on-line gasoline reactor 144 to form non-oxygenated hydrocarbons. In the embodiment of the present embodiment, a modified zeolite-shaped catalyst is utilized in a reactor operating at a temperature of about 450° C. and at a pressure of about 200 kPa to convert the dimethyl ether into a mixture of non-oxygenated hydrocarbons. The reaction conditions provided preferably produce non-oxygenated hydrocarbon having a carbon skeleton ranging in size from $C_5$ to $C_{12}$ among other compounds, thus forming a second mixture 150.

The second mixture 150 emerging from the on-line gasoline reactor 144 is forwarded to a distillation column 146. The liquids which condense are then separated by the column 146 into water and hydrocarbons, and gases, such as un-reacted dimethyl ether from the on-line gasoline reactor 144 which emerges from the top of the column. Hydrocarbons having a carbon skeleton of $C_4$ 72 or less are sent back to the reformer 130 to be reprocessed (not shown). Non-oxygenated hydrocarbons having a carbon skeleton of $C_5$ to $C_{12}$ 85 are forwarded to a gasoline storage vessel 148 where they are collected. Un-reacted DME emerging from the distillation column 146 may optionally be recycled back to the on-line gasoline reactor 144 as is shown at 152 of FIG. 3.

The hydrocarbons having a carbon skeleton of $C_4$ or less and $C_{13}$ 72 or greater are recycled back to the reformer 130 (not shown) to be converted into carbon monoxide, hydrogen and carbon dioxide and join into the second cleaned synthesis gas stream 78 as they emerge from the reformer 130. The hydrocarbon products having a carbon skeleton of $C_5$ to $C_{12}$ alkanes 85 are then removed from the process and sent to storage 148.

Those of skill in the art will recognize certain modifications, permutations, additions and sub-combinations thereof of parts noted herein. While a process for producing hydrocarbon products having a carbon skeleton of $C_5$ to $C_{12}$ alkanes from organic feedstocks has been described for what are presently considered the preferred embodiments, the invention is not so limited. To the contrary, the invention is intended to cover various modifications and equivalent arrangements included within the spirit and scope of the appended claims.

What is claimed is:

1. A process for producing a $C_5$ to $C_{12}$ hydrocarbon fuel from organic material, comprising:
   a) applying a heat source to heat an organic feedstock and oxygen at substoichiometric conditions to a temperature sufficient for partial combustion of said organic feedstock to occur and then ceasing application of said heat source once partial combustion has commenced;
   b) partially combusting said organic feedstock so as to produce a synthesis gas stream, said synthesis gas stream containing at least carbon monoxide, carbon dioxide and hydrogen;
   c) substantially removing unwanted solid and liquid matter comprising oxides, ash and hydrocarbons having a carbon skeleton of greater than $C_{10}$ from said synthesis gas stream to produce a first cleaned synthesis gas stream containing at least carbon monoxide, carbon dioxide and hydrogen;

d) compressing said first cleaned synthesis gas stream and substantially removing water;
e) conditioning and further cleaning the first cleaned synthesis gas stream by substantially removing inorganic elements and inorganic compounds from said first cleaned synthesis gas stream to provide a second cleaned synthesis gas stream containing at least carbon monoxide, carbon dioxide and hydrogen;
f) selectively removing carbon dioxide from said second cleaned synthesis gas stream;
g) catalytically treating said second cleaned synthesis gas stream to produce a first mixture containing at least carbon monoxide, hydrogen and dimethyl ether;
h) collecting said dimethyl ether from said first mixture;
i) catalytically reacting said dimethyl ether to produce a second mixture containing at least alkanes; and
j) selectively obtaining said alkanes having from a $C_5$ to $C_{12}$ skeleton from said second mixture.

2. The process for producing a $C_5$ to $C_{12}$ hydrocarbon fuel from organic material as defined in claim 1, wherein the hydrocarbons having a carbon skeleton of greater than $C_{10}$ are light oils, tar or olefins.

3. The process for producing a $C_5$ to $C_{12}$ hydrocarbon fuel from organic material as defined in claim 1, wherein step (e) further comprises removing at least a portion of the alkanes, alkenes and alkynes contained in said first cleaned synthesis gas stream and reacting said removed alkanes, alkenes and alkynes in a reformer to produce at least carbon monoxide, carbon dioxide and hydrogen.

4. The process for producing a $C_5$ to $C_{12}$ hydrocarbon fuel from organic material as defined in claim 3, wherein the reformer is an autothermal reformer and wherein the alkanes, alkenes and alkynes are reacted in the reformer at a temperature of from about 950° C. to about 1100° C. and at a pressure of less than about 9790 kpa.

5. The process for producing a $C_5$ to $C_{12}$ hydrocarbon fuel from organic material as defined in claim 1, wherein the carbon dioxide is selectively removed from the second cleaned synthesis gas stream by an acid/gas carbon dioxide removal process.

6. The process for producing a $C_5$ to $C_{12}$ hydrocarbon fuel from organic material as defined in claim 1, wherein the second cleaned synthesis gas stream is catalytically treated to produce the first mixture comprising at least carbon monoxide, hydrogen and dimethyl ether using a base metal catalyst.

7. The process for producing a $C_5$ to $C_{12}$ hydrocarbon fuel from organic material as defined in claim 6, wherein the second cleaned synthesis gas stream is catalytically treated to produce the first mixture comprising at least carbon monoxide, hydrogen and dimethyl ether using the base metal catalyst at a temperature of from about 225° C. to about 300° C. and at a pressure of 2.5 Mpa to 7.5 Mpa; the base metal catalyst being a nickel catalyst, a copper catalyst, a zinc catalyst, or an iron catalyst.

8. The process for producing a $C_5$ to $C_{12}$ hydrocarbon fuel from organic material as defined in claim 1, wherein the dimethyl ether in the first mixture is catalytically treated to produce a second mixture containing at least alkanes using a zeolite catalyst.

9. The process for producing a $C_5$ to $C_{12}$ hydrocarbon fuel from organic material as defined in claim 8, wherein the zeolite catalyst has a ratio of silica to alumina of from about 298:1 to about 2000:1.

10. The process for producing a $C_5$ to $C_{12}$ hydrocarbon fuel from organic material as defined in claim 9, wherein the dimethyl ether in the first mixture is catalytically treated at a temperature of from about 350° C. to about 450° C. and at a pressure of from about 140 kpa to about 350 kpa.

11. The process for producing a $C_5$ to $C_{12}$ hydrocarbon fuel from organic material as defined in claim 1, wherein the $C_5$ to $C_{12}$ alkanes are selectively obtained from the second mixture by distillation.

12. The process for producing a $C_5$ to $C_{12}$ hydrocarbon fuel from organic material as defined in claim 1, wherein the second mixture further contains alkenes, alkynes, aromatic compounds, or naphthalenes.

13. The process for producing a $C_5$ to $C_{12}$ hydrocarbon fuel from organic material as defined in claim 12, wherein the alkenes, alkynes, aromatic compounds, or naphthalenes are selectively obtained from the second mixture by distillation.

14. The process for producing a $C_5$ to $C_{12}$ hydrocarbon fuel from organic material as defined in claim 1, wherein step (f) further comprises using a water/gas shift reaction.

15. The process for producing a $C_5$ to $C_{12}$ hydrocarbon fuel from organic material as defined in claim 14, wherein the water/gas shift reaction increases the ratio of hydrogen to carbon monoxide.

16. The process for producing a $C_5$ to $C_{12}$ hydrocarbon fuel from organic material as defined in claim 15, wherein the ratio of hydrogen to carbon monoxide is from about 1:1 to about 1:2.

17. The process for producing a $C_5$ to $C_{12}$ hydrocarbon fuel from organic material as defined in claim 1, wherein the organic feedstock is a solid, a gas or a liquid.

18. A process for producing a $C_5$ to $C_{12}$ hydrocarbon fuel from organic material comprising:
   a) applying a heat source to heat an organic feedstock and oxygen at substoichiometric conditions up to a temperature of about 800° C. and then ceasing application of said heat source once partial combustion in an exothermic reaction has commenced;
   b) partially combusting said organic feedstock without continuous application of an external heat source so as to produce a synthesis gas stream, said synthesis gas stream containing at least carbon monoxide, carbon dioxide and hydrogen;
   c) substantially removing unwanted solid and liquid matter comprising oxides, ash and hydrocarbons having a carbon skeleton of greater than $C_{10}$ from said synthesis gas stream to produce a first cleaned synthesis gas stream containing at least carbon monoxide, carbon dioxide and hydrogen;
   d) compressing said first cleaned synthesis gas stream and substantially removing water;
   e) removing at least a portion of the alkanes, alkenes and alkynes from said first cleaned synthesis gas stream;
   f) reacting said removed alkanes, alkenes and alkynes of step e) with a catalyst to produce a supplemental gas stream containing at least carbon monoxide, carbon dioxide and hydrogen;
   g) removing inorganic elements and inorganic compounds from said first cleaned synthesis gas stream to provide a second cleaned synthesis gas stream containing at least carbon monoxide, carbon dioxide and hydrogen;
   h) merging said second cleaned synthesis gas stream with said supplemental gas stream;
   i) selectively removing carbon dioxide from said second cleaned synthesis gas stream merged with said supplemental gas stream;
   j) catalytically treating said second cleaned synthesis gas stream merged with said supplemental gas stream to produce a first mixture containing at least carbon monoxide, hydrogen and dimethyl ether;
k) collecting said dimethyl ether from said first mixture;
l) catalytically reacting said dimethyl ether to produce a second mixture containing at least alkanes; and
m) selectively obtaining said alkanes having from a $C_5$ to $C_{12}$ skeleton from said second mixture.

19. A process for producing a $C_5$ to $C_{12}$ hydrocarbon fuel from organic material comprising:
a) forming a first synthesis gas stream by the steps of
  (i) applying a heat source to heat an organic feedstock and oxygen at substoichiometric conditions up to a temperature of about 800° C. and then ceasing application of said heat source once partial combustion in an exothermic reaction has commenced,
  (ii) partially combusting said organic feedstock without continuous application of a heat source so as to produce a synthesis gas stream, said synthesis gas stream containing at least carbon monoxide, carbon dioxide and hydrogen,
  (iii) substantially removing unwanted solid and liquid matter comprising oxides, ash and hydrocarbons having a carbon skeleton of greater than $C_{10}$ from said synthesis gas stream to produce a first cleaned synthesis gas stream containing at least carbon monoxide, carbon dioxide and hydrogen;
  (iv) recycling and enjoining said hydrocarbons having a carbon skeleton greater than $C_{10}$ to step a)(ii) for partial combustion,
  (v) compressing said first cleaned synthesis gas stream and substantially removing water, and
  (vi) removing at least a portion of the alkanes, alkenes and alkynes from said first cleaned synthesis gas stream;
b) forming a second cleaned synthesis gas stream by the steps of
  (i) reacting said removed alkanes, alkenes and alkynes of step a)(vi) with a catalyst to produce at least carbon monoxide, carbon dioxide and hydrogen, and
  (ii) selectively removing carbon dioxide from said second cleaned synthesis gas stream;
c) merging said first cleaned synthesis gas stream and said second cleaned synthesis gas stream so as to provide a merged cleaned synthesis gas stream;
d) catalytically treating said merged synthesis gas stream to produce a first mixture containing at least carbon monoxide, hydrogen and dimethyl ether;
e) collecting said dimethyl ether from said first mixture and recycling said carbon monoxide back into said second cleaned synthesis gas stream for additional catalytic treatment;
f) catalytically reacting said dimethyl ether to produce a second mixture containing at least alkanes; and
g) selectively obtaining said alkanes having from a $C_5$ to $C_{12}$ skeleton from said second mixture.

* * * * *